United States Patent [19]

Natwick et al.

[11] Patent Number: 5,219,279
[45] Date of Patent: Jun. 15, 1993

[54] VOLUMETRIC PUMP WITH PUMP PLUNGER SUPPORT AND METHOD

[75] Inventors: Vernon R. Natwick, Los Altos; Michael W. Lawless, Boulder Creek, both of Calif.

[73] Assignee: Abbott Laboratories, Abbott Park, Ill.

[21] Appl. No.: 916,426

[22] Filed: Jul. 17, 1992

Related U.S. Application Data

[62] Division of Ser. No. 742,623, Aug. 8, 1991, Pat. No. 5,158,437, which is a division of Ser. No. 494,210, Mar. 15, 1990, Pat. No. 5,055,001.

[51] Int. Cl.$^5$ .................. F04B 43/08; F16H 25/08
[52] U.S. Cl. ............................. 417/479; 74/55; 92/140
[58] Field of Search .................. 417/474–479; 92/161, 140; 74/55

[56] References Cited

U.S. PATENT DOCUMENTS

| | | | |
|---|---|---|---|
| 447,964 | 10/1891 | Mentzel | 74/55 |
| 4,159,651 | 7/1979 | MacPhee | 74/55 |
| 5,039,279 | 8/1991 | Natwick et al. | 417/479 |
| 5,116,203 | 5/1992 | Natwick et al. | 417/474 |

Primary Examiner—Richard A. Bertsch
Assistant Examiner—Peter Korytnyk
Attorney, Agent, or Firm—Christensen, O'Connor, Johnson & Kindness

[57] ABSTRACT

A volumetric pump and method for displacing a predetermined quantity of fluid at a predefined cracking pressure, independent of supply and output pressures. The volumetric pump (30) includes an inlet cracking valve (46), an outlet cracking valve (52), and a plunger (48) for displacing fluid a pumping from a pumping portion (34b) of flexible tubing (34) that extends through the volumetric pump. The pumping portion of the flexible tube fills with liquid when the inlet cracking valve is fully opened and is urged to expand by jaws (236) on pivotally-mounted arms (234). The arms are forced to pivot, as tubing reshaper rollers (160), disposed on the plunger, roll along the inner surface (232) of each arm. During a pumpback-pressurization segment of the pumping cycle, the inlet cracking valve applies a cracking force to the flexible tubing, while the plunger compresses the pumping portion of the flexible tubing sufficiently to develop a cracking pressure that displaces excess fluid back through the inlet cracking valve toward a container (32). After the excess fluid has been forced from the pumping portion of the flexible tubing, a pumping segment of the cycle begins, wherein the inlet cracking valve closes fully and the outlet cracking valve applies a cracking force to compress the flexible tubing. Fluid is then forced by the plunger from the pumping portion of the flexible tubing into a distal portion (34c). The volumetric pump compensates for variations in elasticity of the flexible tubing that would otherwise cause variations in the cracking pressure, using balance blocks (42 and 58). A volumetric pump (400) for use with a cassette (300) comprises a second embodiment of the volumetric pump, in which inlet and outlet cracking valves are defined in respect to the forces applied by actuators against a flexible membrane (340) in the cassette, while a plunger (326) displaces fluid from a pumping chamber (360) in the cassette. Volumetric pump (400) applies appropriate forces to an inlet valve actuator (318) and an outlet valve actuator (332) to achieve cracking and closure forces, just as in the first embodiment.

10 Claims, 17 Drawing Sheets

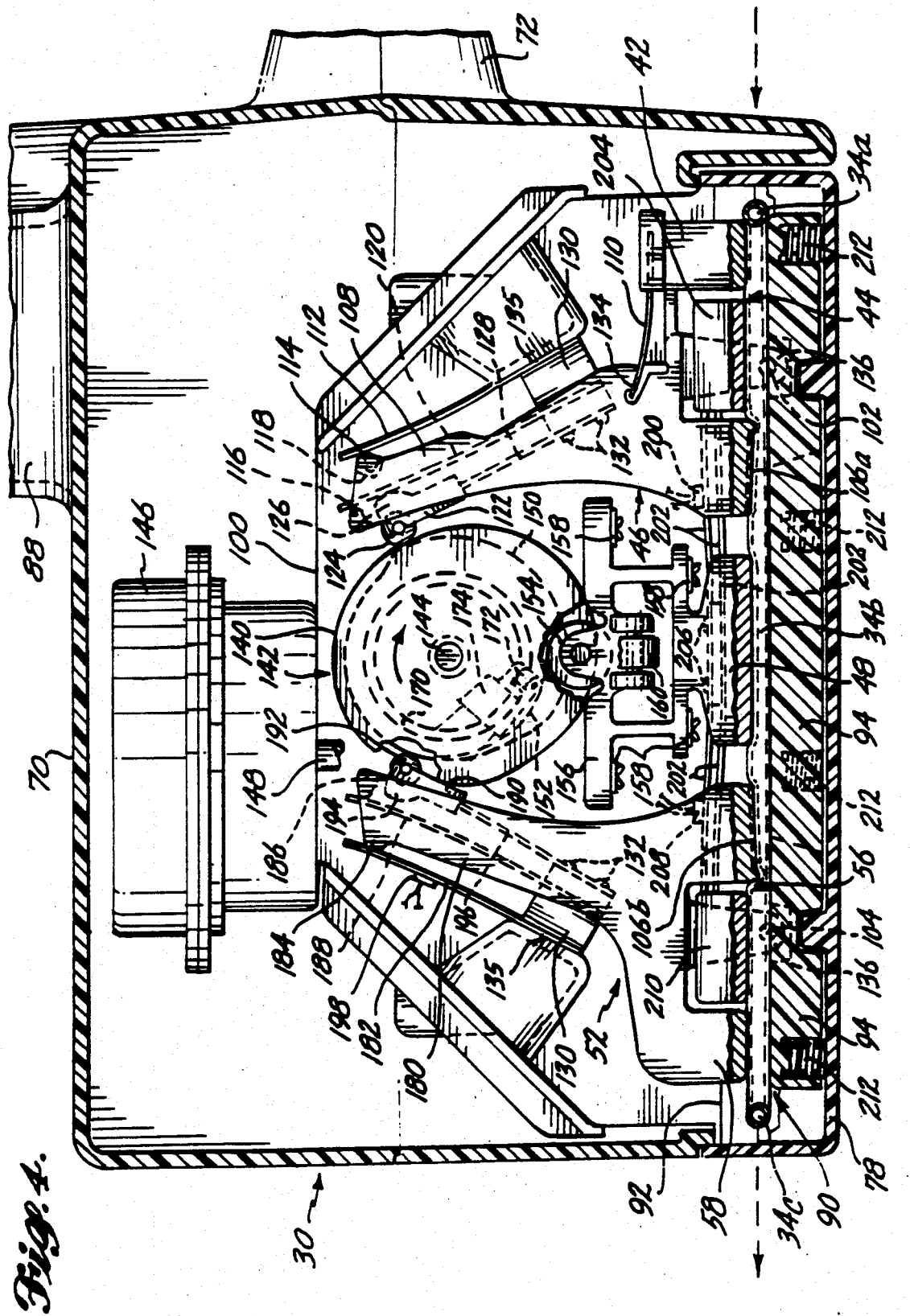

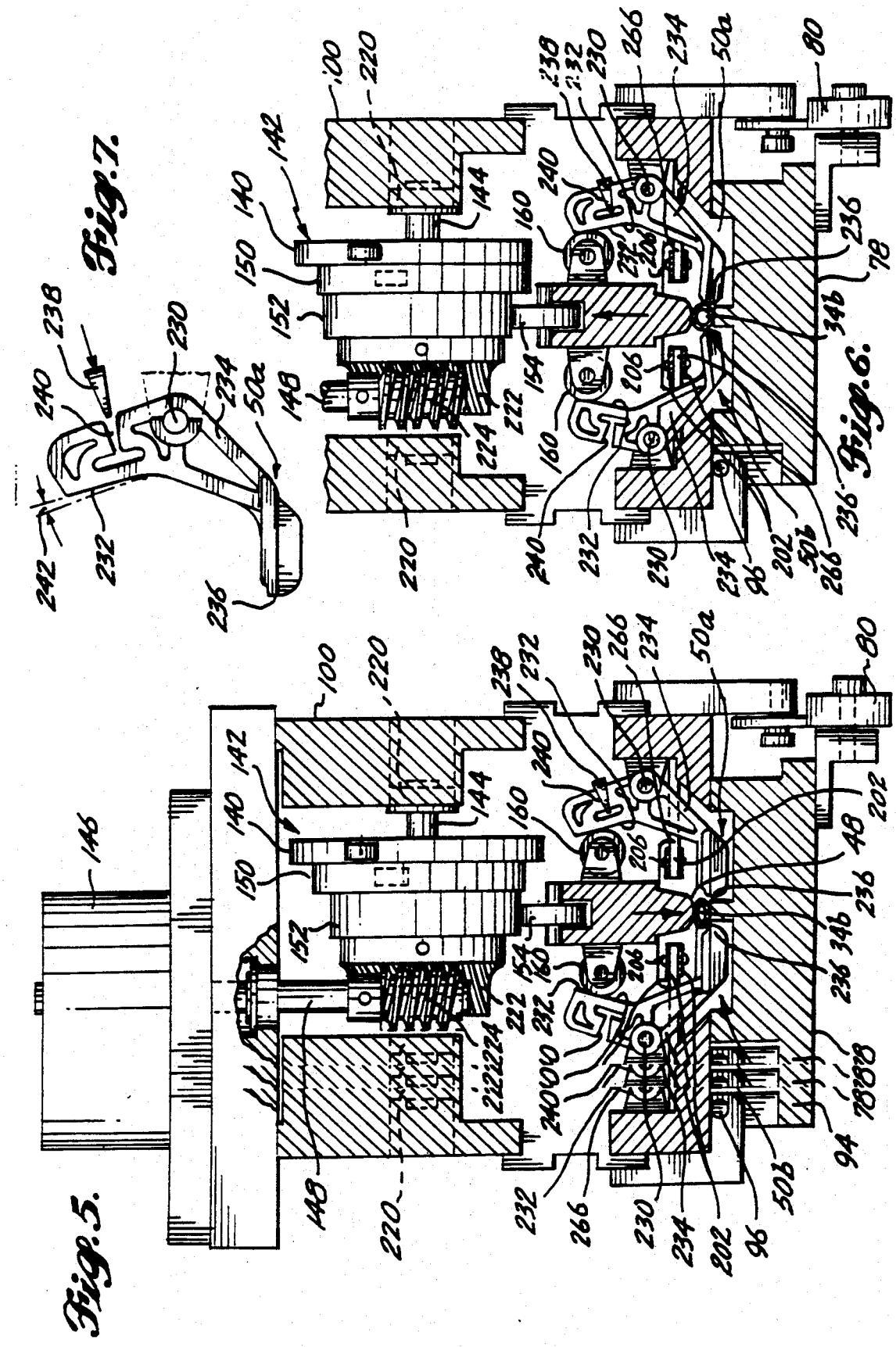

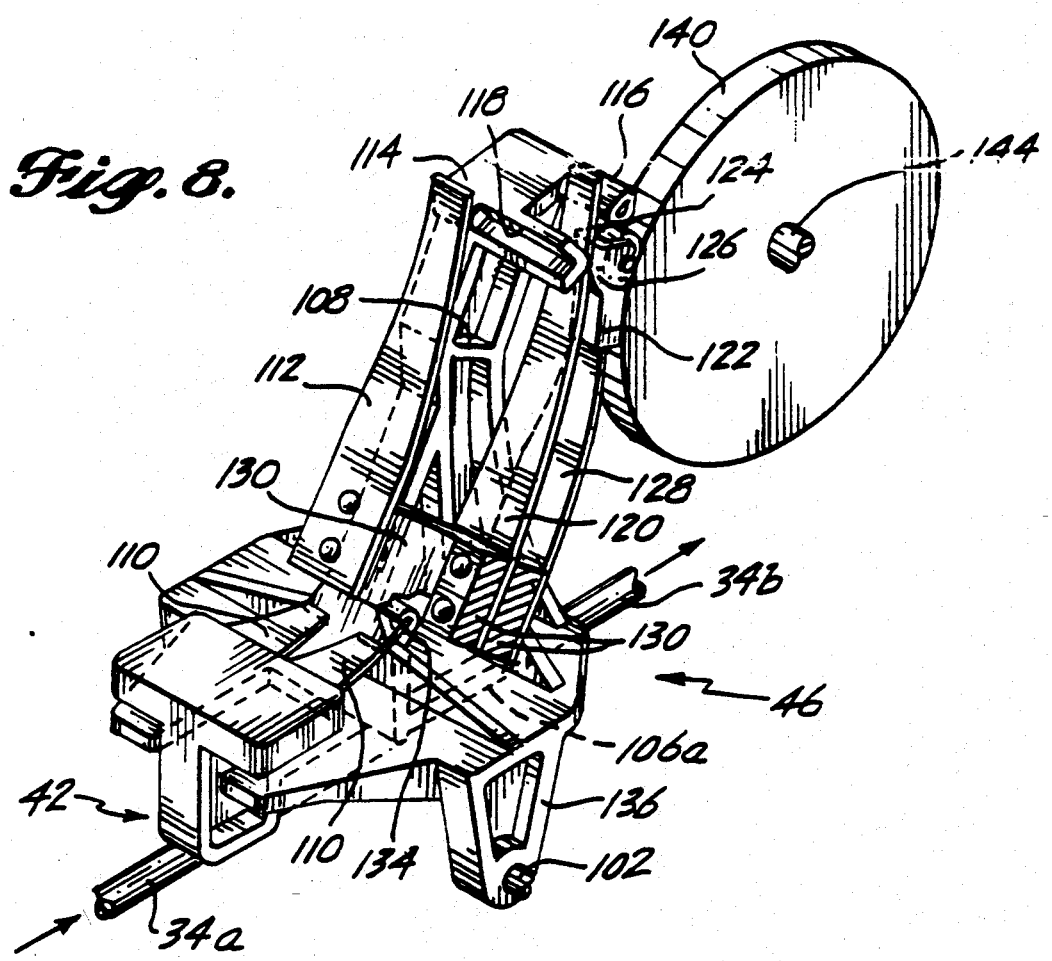
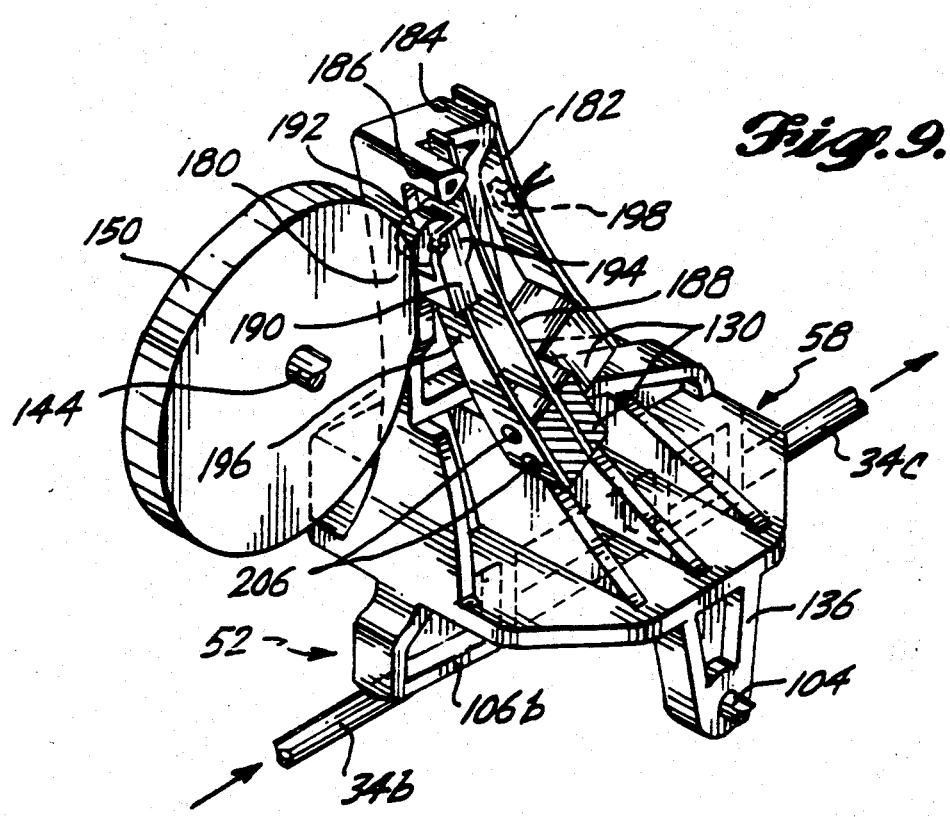

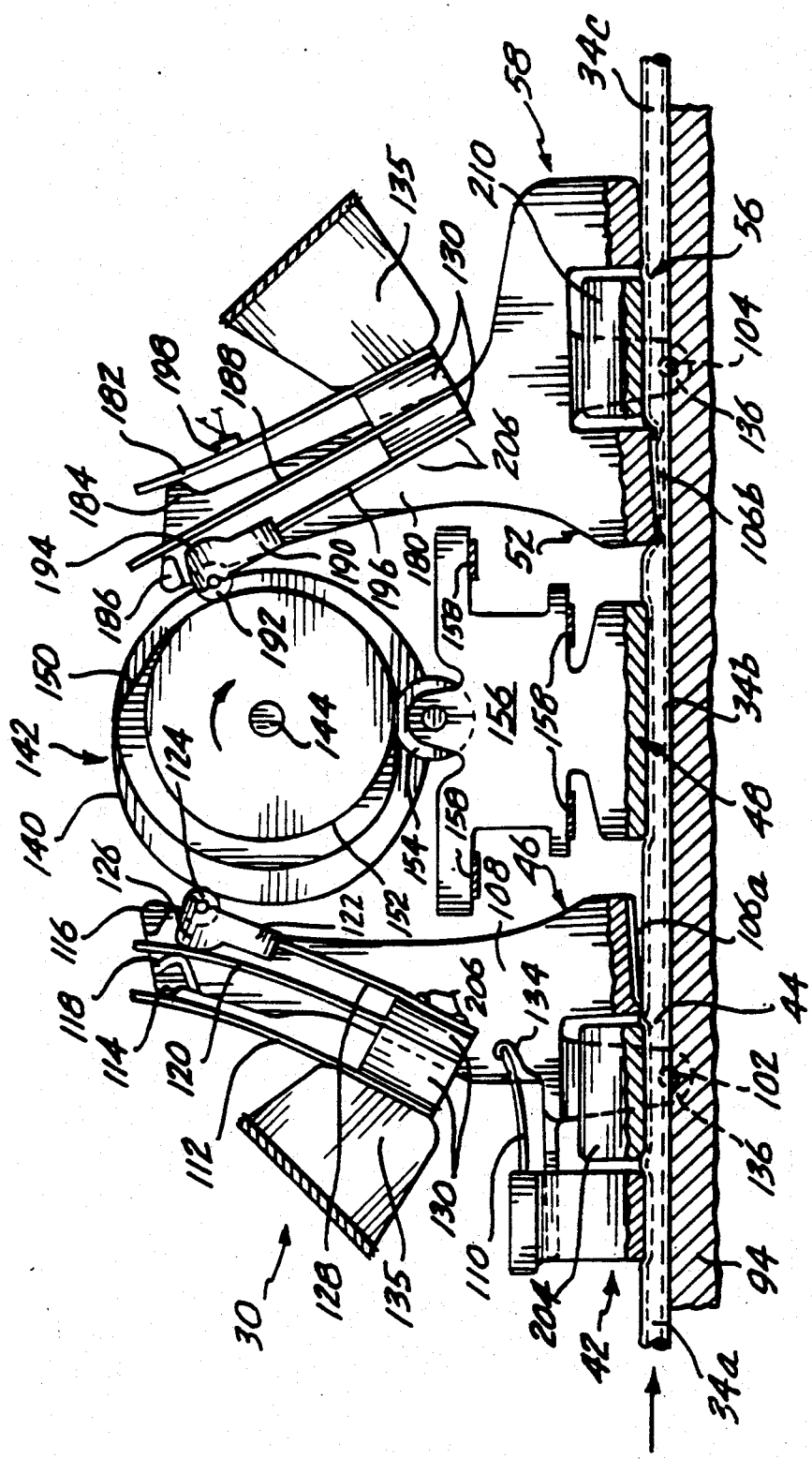

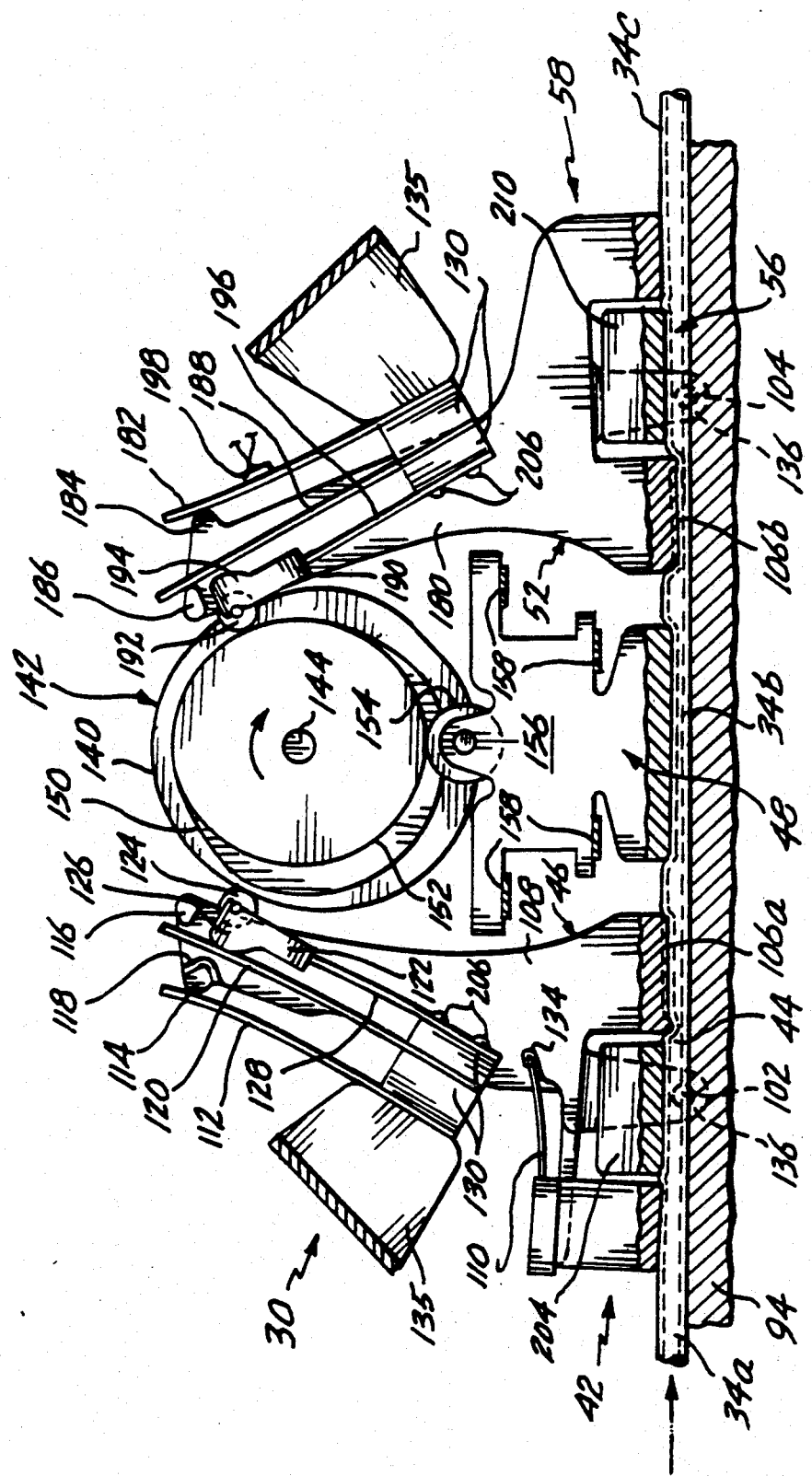

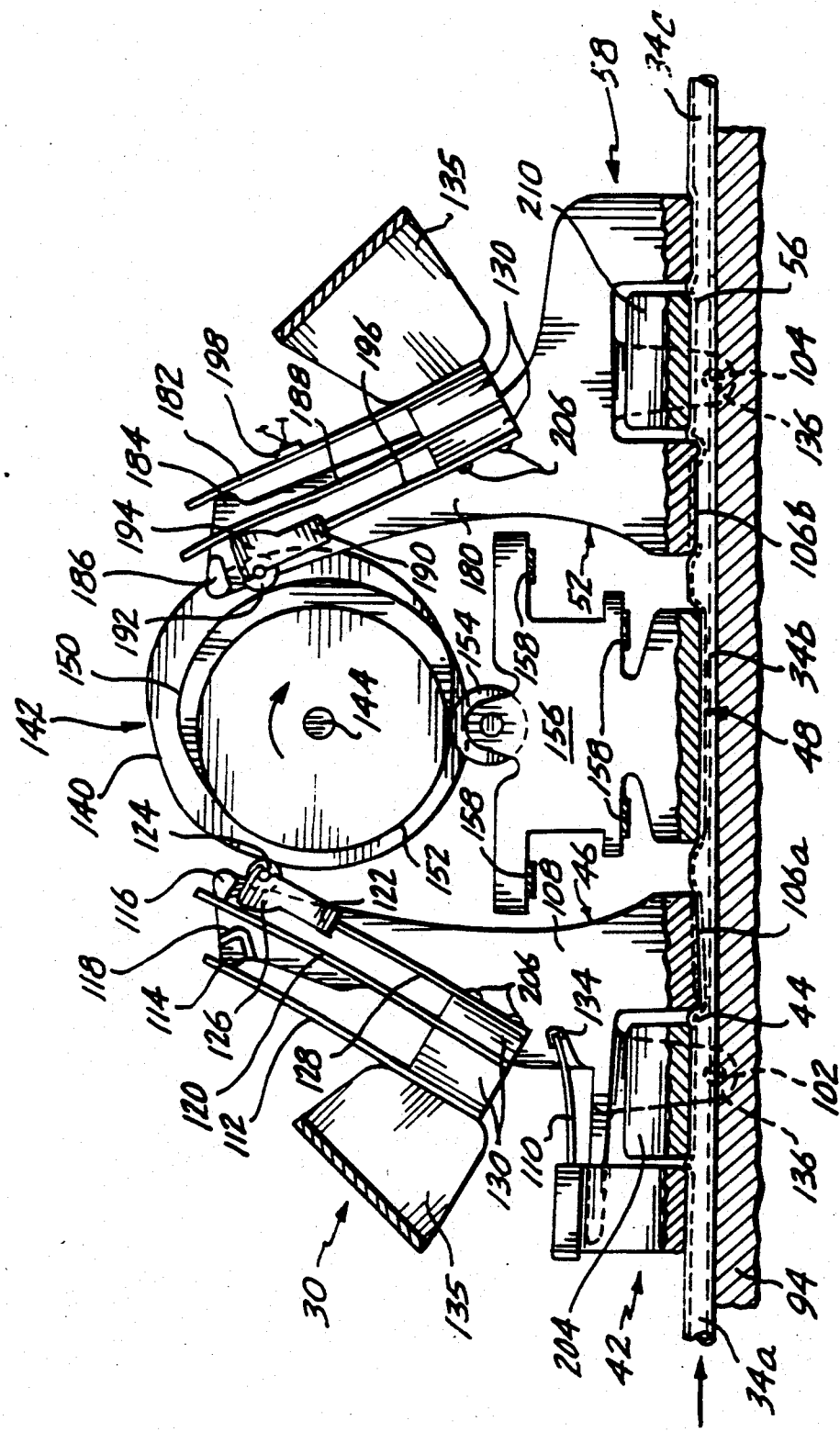

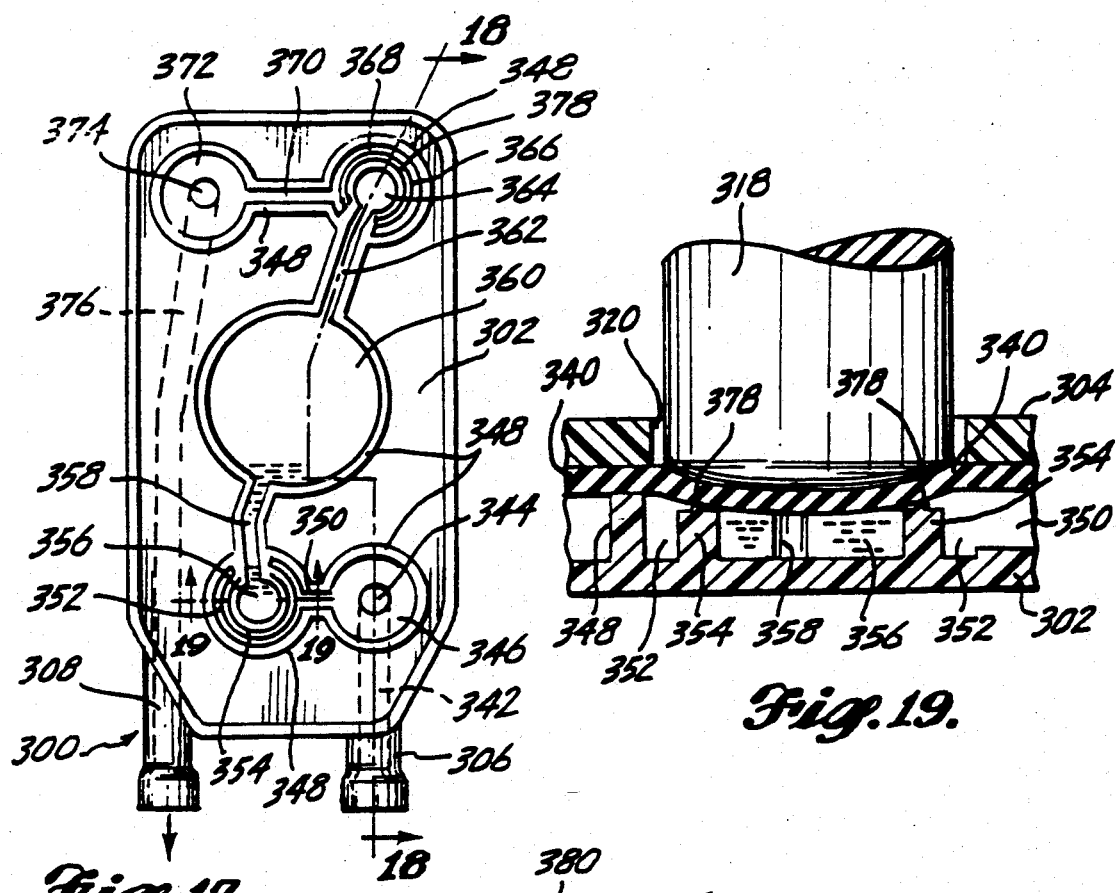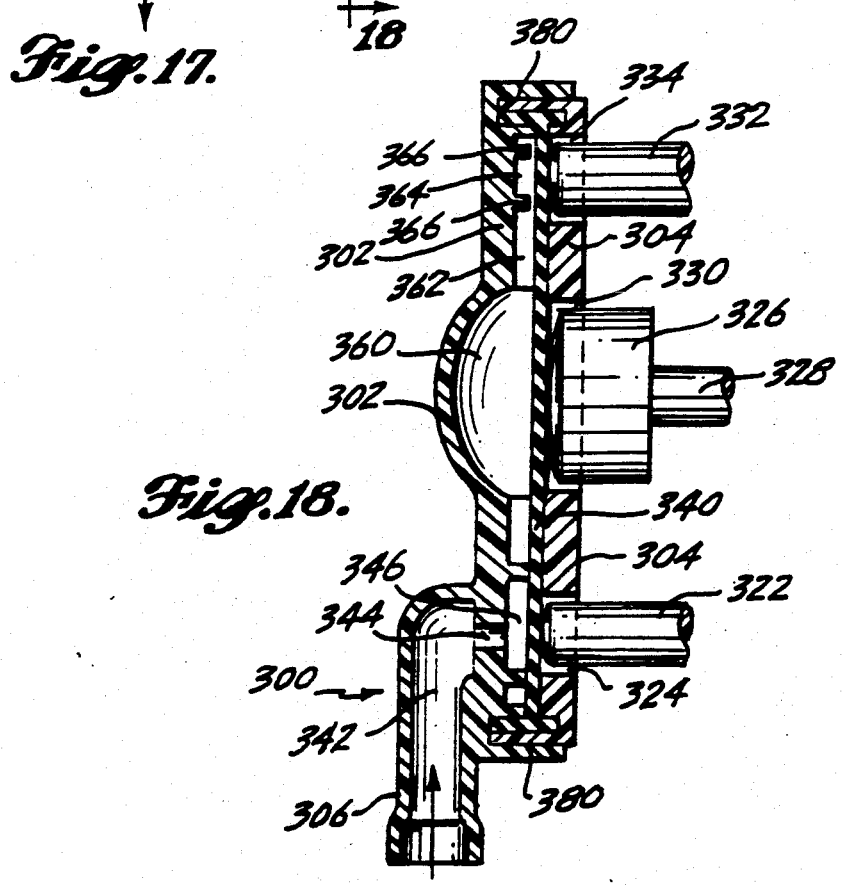

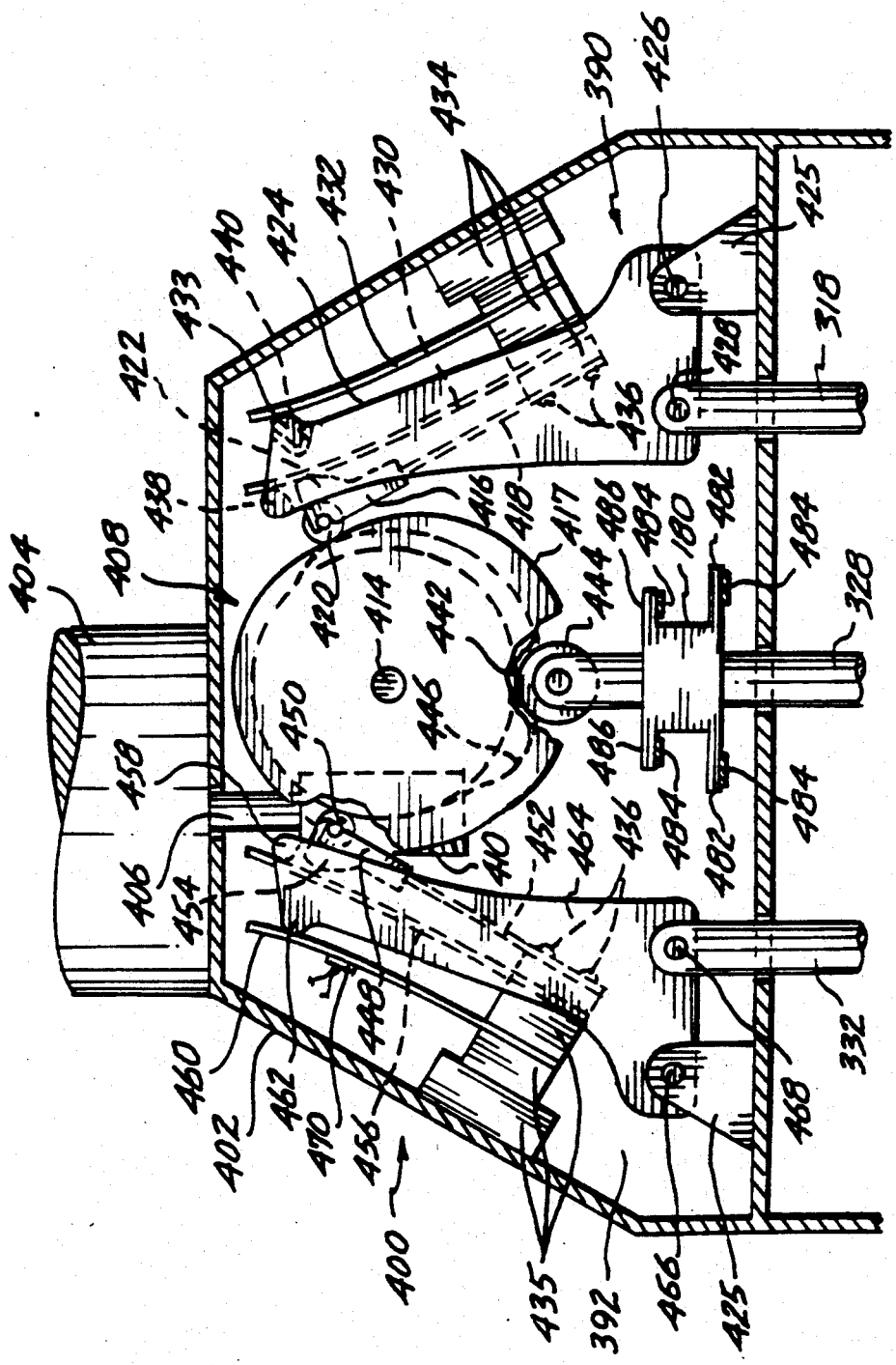

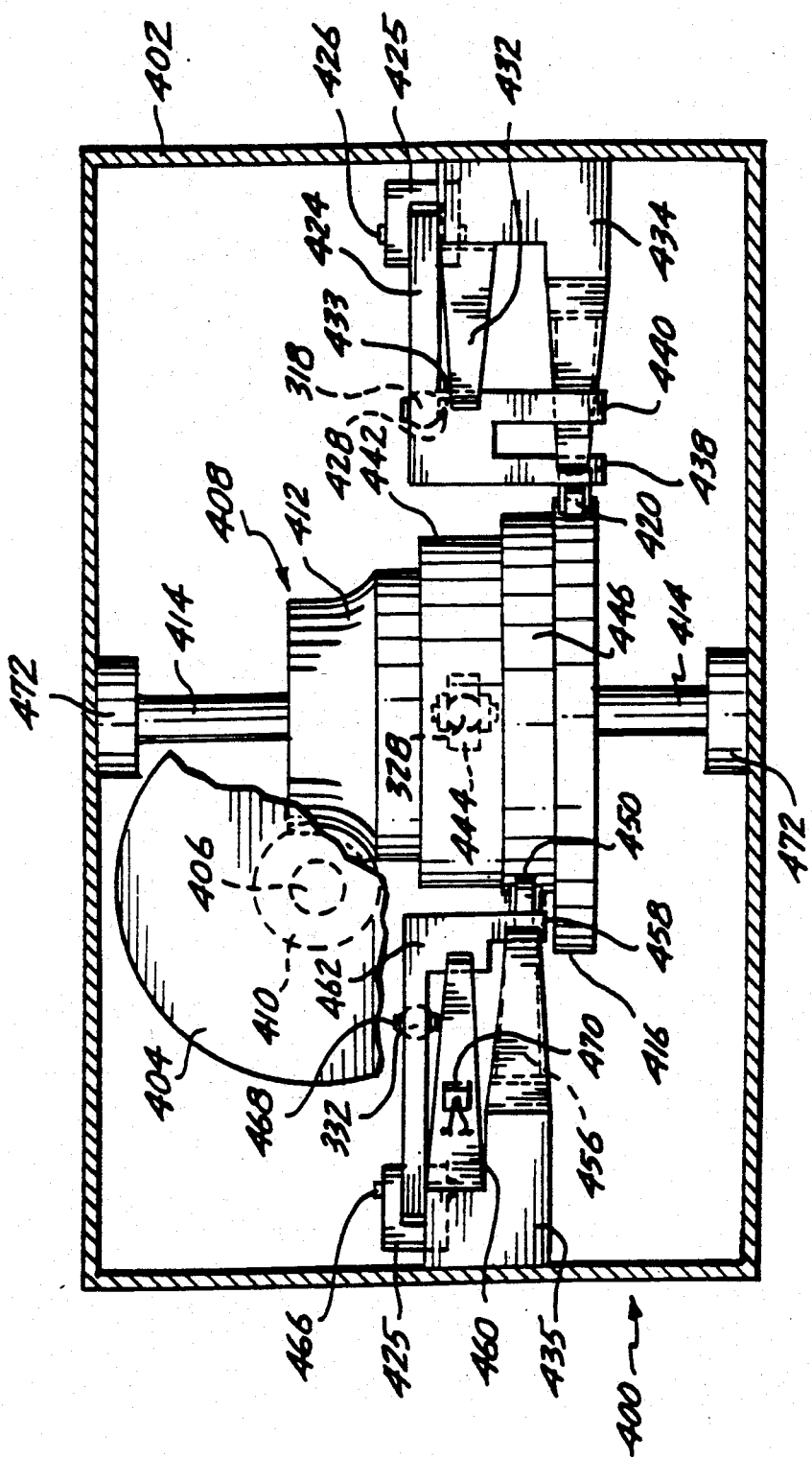

VOLUMETRIC PUMP WITH PUMP PLUNGER SUPPORT AND METHOD

This is a divisional of now U.S. Pat. No. 5,158,437, the prior application Ser. No. 742,623, filed Aug. 8, 1991, which in turn is a divisional of U.S. Pat. No. 5,055,001, issued Oct. 8, 1992, the benefit of the filing dates of which are hereby claimed under 35 U.S.C. § 120.

TECHNICAL FIELD

This invention generally pertains to a positive displacement volumetric pump, and specifically, to a volumetric pump in which a plunger acts on a flexible member to displace fluid from a chamber.

BACKGROUND OF THE INVENTION

Intravenous infusion of medicinal liquids has traditionally been accomplished using drip regulated, gravity flow systems. However, it is generally recognized that a more precisely regulated flow of drug to the patient can be administered with a pump. Because of their simplicity and ease of use, peristaltic pumps are often used for this purpose. A gravity flow system is readily converted to a peristaltic pump infusion system by threading the drug delivery or intravenous (IV) line, which is attached to the drug container, through the peristaltic pump. The pump then controls the rate at which the drug is delivered to the patient.

A peristaltic pump displaces liquid by repetitively compressing a section of the flexible tube comprising the IV line. This line is threaded through a channel formed in the pump and extends unbroken, from the drug container to the patient. In one type of peristaltic pump, the channel is curved around a central axis. A rotating arm with rollers fixed on each end compresses the section of tubing disposed within the channel, advancing the rollers along the longitudinal axis of the tubing as the arm rotates about the central axis. Liquid within the tubing is thus forced ahead of the advancing roller along the internal passage in the line.

Another type of peristaltic pump has a linear channel in which the IV line is threaded and is thus referred to as a linear (or traveling wave) peristaltic pump. The linear peristaltic pump includes a plurality of finger-like plungers that are sequentially actuated by cams mounted along a motor driven shaft. Liquid within the section of tubing that extends along the linear channel is advanced along the tubing's longitudinal axis by the advancing wave-like compression of the fingers. An example of such a pump is disclosed in U.S. Pat. No. 4,479,797.

Inlet and outlet valves and a single liquid displacement plunger are used in another type of peristaltic pump. Each pumping cycle in this type of pump begins with the outlet valve closed and the inlet valve open. Fluid flows from the source container into a short section of tubing that is disposed between the inlet and outlet valve. After this section of tubing has filled with liquid, the inlet valve closes and the outlet valve opens. The plunger then compresses the short section of tubing between the valves, displacing the liquid contained therein, and forcing it from the pump. U.S. Pat. No. 4,559,038 discloses a peristaltic pump of this type.

Cassette pumps are also frequently used in administering medicinal fluids to a patient and normally provide a more accurate rate of fluid flow than a peristaltic pump. In a cassette pump, a cassette comprising a plastic housing that includes a pumping chamber and inlet and outlet valves, is connected via a disposable tube set to a drug container. The cassette is inserted into an appropriate device designed to drive the cassette and administer fluid at a controlled rate. The pumping device includes an inlet valve actuator, an outlet valve actuator, and a pumping plunger. Inside the cassette, passages connect the inlet valve and the outlet valve to the pumping chamber; a flexible membrane, which is sealed between two halves of the plastic housing, interrupts fluid flow through inlet and outlet valve openings formed in the housing when the membrane is deformed by the inlet and outlet valve actuators. The plunger acts on the flexible membrane covering the pumping chamber in the cassette to force liquid past the open outlet valve and through an outlet port of the cassette. An example of a cassette pump is disclosed in commonly assigned U.S. Pat. No. 4,818,186.

The rate at which fluid is delivered by each type of positive displacement pump discussed above is normally controlled by the rate at which the pump operates, e.g., the rotational rate of the rotating arm in that type of peristaltic pump. Furthermore, the accuracy with which a given rate or volume of fluid flow can be achieved by these pumps is dependent upon the pressure of the fluid at the input of the pump and the back pressure at its output. Since both the flexible tubing (in the peristaltic pumps) and the flexible membrane (in the cassette) define a compliant pumping chamber, the volume of fluid that fills the pumping chamber is affected by the head pressure of the fluid from the drug container. Similarly, the volume of fluid delivered at the output of the pump depends on the back pressure of the fluid downstream of the outlet. The cassette pump and the single plunger type of peristaltic pump, both of which have positive closure inlet and outlet valves, are particularly sensitive to head and back pressure because the volume of the pumping chamber disposed between the valves and the amount of fluid that fills the chamber generally must be constant to provide an accurate and consistent rate of flow from the pump.

Several other parameters can affect the accuracy of fluid flow delivered by specific types of positive displacement pumps. For example, when the compression force is removed from the tubing in a peristaltic pump, the tubing must recover to a defined and consistent internal diameter to insure that the same volume of fluid is delivered in each pump cycle. If the volume of the passage defining the pumping chamber changes over time, for example, due to changes in the tubing elasticity, the pump's flow rate will also change. Inexpensive polyvinyl chloride (PVC) tubing, commonly used for disposable tube sets in medical IV applications, is known to experience changes in elasticity over time and with repetitive compression of the tubing, thereby affecting the extent to which the tubing recovers when a compression force is removed.

In the single plunger type of peristaltic pump, the plunger should compress the tubing uniformly and consistently with each pumping stroke to provide an accurate and consistent rate of fluid flow from the pump. The plunger mounting assembly must permit the plunger to move freely back and forth along a reciprocation axis, yet should prevent it from twisting or moving laterally away from this axis, because such movement can change the compression stroke volumetric displacement. Since the plunger is typically driven by a rotating cam, the mounting assembly should also provide a biasing force to maintain the plunger in contact with the cam surface, preferably without introducing sliding friction or using helical springs. Most prior art plunger mounting assemblies do not address all of these concerns.

Due to the potential safety concerns involved in administering medicinal fluids intravenously to a patient, an infusion pump should include an air-in-line sensor to detect large air bubbles within the pump and stop the pump before such bubbles are infused into the patient's circulatory system. Provision should also be made to detect when a drug container becomes empty or a supply line connected to the container occluded. If the flow of fluid from the pump is interrupted for any reason, the pump should be shut off and an alarm sounded to alert medical personnel. Ideally, these functions should be integrated into the pump, and are in some prior art pumps. However, virtually none of the available peristaltic pumps currently provide both of these safety-related features.

In consideration of these problems that exist with the prior art pumps, it is an object of the present invention to provide a positive displacement pump in which the volume and rate of delivery of fluid from the pump is substantially unaffected by variations in the pressure of fluid supplied to the pump. Another object of this invention is to provide a pump in which the volume and the rate fluid is delivered from the pump is substantially unaffected by variations in fluid pressure downstream of the pump. Yet a further object is to provide a positive displacement fluid pump that delivers fluid to an output port of the pump at a predefined pressure. Still a further object of the invention is to provide a spring-biased support for a plunger enabling it to reciprocate freely along a reciprocation axis without sliding friction, while preventing it from twisting or moving laterally away from the reciprocation axis. These and other objects and advantages of the present invention will be apparent from the attached drawings and the Description of the Preferred Embodiments that follows.

SUMMARY OF THE INVENTION

In accordance with the claimed invention, a volumetric pump is adapted to pump a fluid through a set that includes a flexible member, by deforming different portions of the flexible member in a predefined pumping cycle. The portions of the flexible member respectively define a chamber, an inlet passage, and an outlet passage. Deformation of the portion of the flexible member defining the chamber reduces the volume of the chamber and displaces fluid from it. The volumetric pump includes a chassis on which an inlet valve is disposed adjacent to the inlet passage. The inlet valve is positioned to act on an inlet portion of the flexible member to control fluid flow through the inlet passage and exerts a first and a second sealing force on the inlet portion of the flexible member during the pumping cycle. The first sealing force is substantially less than the second sealing force and allows fluid to flow through the inlet passage from the chamber as fluid in the chamber is initially pressurized beyond a predefined level. The second sealing force subsequently interrupts fluid flow through the inlet passage from the chamber, enabling fluid pressurized in the chamber to be forced through the outlet passage.

A plunger disposed on the chassis adjacent the chamber is operative to deform a pumping portion of the flexible member to displace fluid from within the chamber. An outlet valve is disposed on the chassis adjacent the outlet passage and is thus positioned to act on an outlet portion of the flexible member to control fluid flow through the outlet passage. The outlet valve exerts a forward-flow sealing force and a back-flow sealing force on the outlet portion of the flexible member during the pumping cycle. The forward-flow sealing force is substantially less than the back-flow sealing force and allows fluid to flow through the outlet passage from the chamber; however, the back-flow sealing force completely interrupts fluid flow past the outlet valve. Means are also provided for actuating the inlet valve, the outlet valve, and the plunger to deform the portions of the flexible member during the pumping cycle, thereby forcing fluid through the outlet passage at a predetermined rate of fluid delivery.

The means for actuating the valves and plunger comprise a motor, an inlet valve cam, an outlet valve cam, and a pumping cam. A profile on the pumping cam sequentially defines a filling segment, a pumpback-pressurization segment, and a pumping segment. After the chamber is filled with fluid, the inlet valve exerts the first sealing force and the outlet valve blocks fluid flow from the chamber into the outlet passage, enabling fluid pressurized in the chamber to be forced through the inlet passage. The motor rotates the pumping cam from a start position and the pumping cam actuates the plunger to pressurize fluid in the chamber to the predefined level, thus forcing excess fluid in the chamber to backflow through the inlet passage until the pumping cam reaches a rotational position corresponding to the start of a pumping stroke. During the pumping stroke, fluid is again displaced from the chamber by the plunger and forced to flow through the outlet passage as the inlet valve cam causes the inlet valve to close with the second sealing force, thereby preventing fluid flow through the inlet passage. After the pumping stroke is completed, the inlet valve cam causes the inlet valve to open fully, enabling fluid to flow from a source through the inlet passage, again filling the chamber.

At all times, even when the volumetric pump is not pumping fluid, at least one of the inlet and outlet valves blocks fluid flow through the inlet and outlet passages, respectively. The rate at which the motor rotates the inlet, the outlet, and the pumping cams, at least in part, controls the rate at which the fluid is delivered through the outlet passage. To further reduce the rate of fluid delivery, the motor stops rotating the pumping cam for an interval of time at least once during the pumping stroke.

In one embodiment of the volumetric pump, the flexible member comprises a tube and the pumping chamber comprises a portion of the tube disposed between the inlet and the outlet valves. In this embodiment, the plunger partially compresses the tube when the pumping chamber is filled with fluid at the start position of the pumping cam. The volumetric pump further comprises tube-shaping means that are disposed where the plunger compresses the tube and are operative to bias the tube to more completely fill with fluid.

In another embodiment of the volumetric pump, the flexible member comprises a generally planar, elastomeric membrane disposed in a housing. The inlet valve and the outlet valve comprise spring-biased members that act on the membrane to control fluid flow through passages in the housing.

The volumetric pump may include means for determining if fluid is flowing through the outlet valve as the plunger compresses the flexible member. It may also include means for sensing a fluid pressure upstream of the inlet valve and/or downstream of the outlet valve. Due to the compressibility of a gaseous fluid, if the chamber is substantially filled with such a fluid, the pressure developed in the chamber during the pumping cycle is insufficient to force the gaseous fluid past the outlet valve.

A method for preventing variations in a supply pressure from affecting a fluid delivery rate from a pump that includes an inlet valve and an outlet valve, and which displaces fluid from a pumping chamber defined by a flexible member is another aspect of the present invention. The method comprises steps generally consistent with the functions implemented by the elements of the volumetric pump, as described above.

Yet a further aspect of this invention is an apparatus for supporting a reciprocating plunger in a positive displacement pump. The apparatus includes a frame having two spaced-apart members disposed on opposite sides of the plunger. A plurality of pairs of flexures extend between the two spaced-apart members and the plunger, each flexure having a longitudinal axis. The flexures comprising each pair of flexures are aligned substantially parallel to each other. Due to the disposition and spacing of the flexures, the plunger is supported so that it can reciprocate along a reciprocation axis that is generally normal to the longitudinal axes of each pair of flexures, but is constrained by the pairs of flexures so that it does not move transversely in respect to the reciprocation axis.

The flexures are each attached to the spaced-apart members and to the plunger and apply a biasing force to the plunger that is directed along the reciprocation axis. A first pair of the flexures are attached to the plunger at a first level along the reciprocation axis, and a second pair are attached to the plunger at a second level. The first pair of the flexures are spaced apart a first distance, while the second pair are spaced apart a second distance that is substantially different than the first. The flexures bias the plunger along the reciprocation axis against a drive force that displaces the plunger along the reciprocation axis. One pair of the flexures is preferably spaced apart from the other pair so as to prevent rotation of the plunger about a rotation axis that is normal to the reciprocation axis. Each flexure preferably comprises an elongate flat metal spring.

A method of constraining a plunger to move only along a reciprocation axis, preventing it from twisting or moving laterally away from the reciprocation axis, is yet another aspect of the present invention. The method includes steps generally consistent with the functions of the elements of the apparatus for supporting a plunger, as described above.

Still another aspect of the present invention is apparatus for compressing and shaping a flexible tube. This apparatus includes plunger means, mounted to move bidirectionally along a reciprocation axis. The plunger means periodically compress the flexible tube to displace a fluid from an interior passage disposed within the flexible tube and then allow the flexible tube to expand to at least a partially uncompressed condition. Drive means are included for periodically driving the plunger means to move along the reciprocation axis. Tube shaper means are actuated by the motion of the plunger means and are operative to apply a reshaping force against the flexible tube that tends to expand the interior passage to a maximum desired volume.

The tube shaper means comprise a pair of arms that are pivotally mounted on opposite sides of the plunger means. Jaws are disposed on these arms, at each side of a segment of the flexible tube compressed by the plunger means. Also disposed on opposite sides of the plunger means are a pair of rollers that transmit the reshaping force from the plunger means to the pivotally-mounted arms. Thus, the interior passage is expanded by the jaws in synchronization with the plunger means retracting from a position of maximum compression of the flexible tube.

BRIEF DESCRIPTION OF THE DRAWINGS

FIG. 4 is a longitudinal cross section of the pump assembly shown in FIGS. 2 and 3;

FIG. 5 is a schematic transverse cross section of the volumetric pump, illustrating compression of the flexible tube to pump fluid;

FIG. 6 is a schematic cross section of the volumetric pump, illustrating reshaping of the flexible tube to facilitate its filling with fluid;

FIG. 7 is a plan view illustrating the calibration of one of the tube reshaping arms to achieve a desired angular deflection;

FIG. 8 is an isometric view of an inlet cracking valve used in the volumetric pump and a transverse section of a cam assembly that is used to actuate the cracking valve;

FIG. 9 is an analogous view to that of FIG. 8, isometrically showing an outlet cracking valve used in the volumetric pump and a transverse section of the cam assembly that is used to actuate the outlet cracking valve;

FIGS. 10A–10C are cutaway, longitudinal cross sections of the volumetric pump respectively illustrating a fill segment, a pumpback-pressurization segment, and a pumping segment of the pumping cycle;

FIG. 17 is a plan view of the cassette with a front panel and a flexible membrane removed to illustrate a fluid path through the cassette;

FIG. 18 is a cross-sectional view of the cassette, taken generally along section line 18—18 in FIG. 17, but showing the front panel and the flexible membrane;

FIG. 19 is a partial cross-sectional view of the inlet cracking valve in the cassette, taken generally along section line 19—19 in FIG. 17, and showing the front panel and the flexible membrane;

FIG. 20 is a longitudinal cross-sectional view schematically illustrating a volumetric pump drive mechanism for the cassette;

FIG. 21 is a plan view of the volumetric pump drive mechanism shown in FIG. 20;

DESCRIPTION OF THE PREFERRED EMBODIMENTS

The term "volumetric pump" is applied to the present invention because it appropriately emphasizes one of the invention's more important advantages. Specifically, during each pumping stroke, the volumetric pump consistently and repeatedly displaces a defined volume of fluid at a defined pressure, thereby ensuring that a desired rate of fluid flow is accurately provided by the pump.

Figure 1:
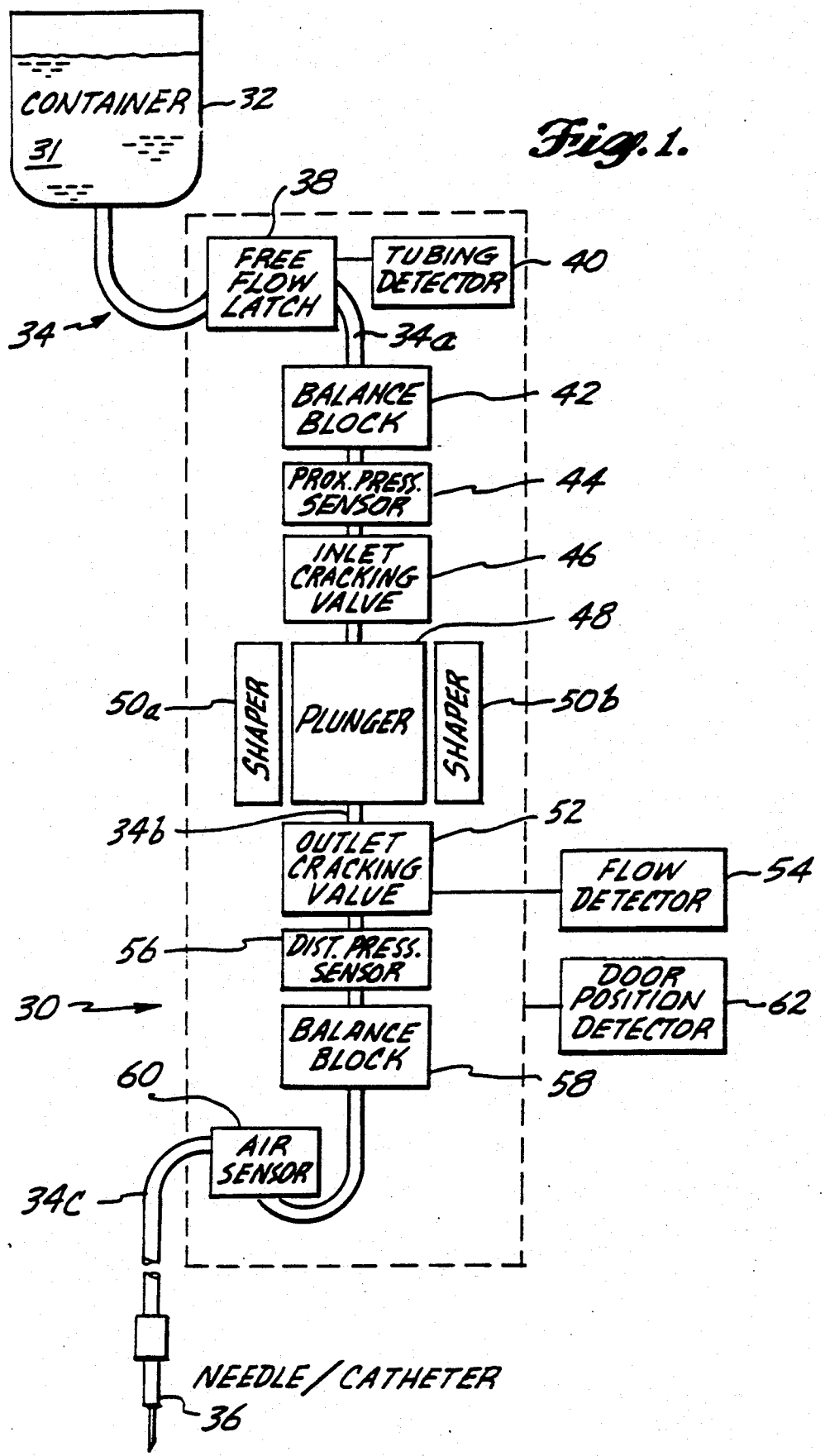
FIG. 1 is a schematic block diagram of a volumetric pump in accordance with the present invention.

In FIG. 1, a volumetric pump in accordance with the present invention is generally illustrated in block diagram at reference numeral 30. Volumetric pump 30 comprises a number of components that are serially arranged along a fluid path through the pump. A liquid 31 that is administered by volumetric pump 30 is supplied from a container 32 through flexible tubing 34. Liquid 31 enters volumetric pump 30 through a proximal portion 34a of the flexible tubing. The fluid path continues through a pumping portion 34b and exits the pump through a distal portion 34c of the flexible tubing. Distal portion 34c of the flexible tubing is connected to a needle/catheter 36 that is used to introduce liquid 31 output from the pump intravenously into a patient. Of course, volumetric pump 30 may also be used in other applications wherein distal portion 34c of the flexible tubing is connected to some other apparatus disposed downstream of volumetric pump 30.

Flexible tubing 34 is continuous, but for purposes of this disclosure, is referred to as divided into the proximal, pumping, and distal portions 34a, 34b, and 34c, respectively; preferably, it comprises a polyvinyl chloride (PVC) disposable tube set, such as is customarily used to administer fluids intravenously to a patient. The tubing may have a 0.137" O.D. and 0.100" I.D.

In this application of the volumetric pump, it is desirable to prevent free flow of liquid 31 from container 32 into the patient. For this reason, volumetric pump 30 includes a free flow latch 38, which clamps proximal portion 34a of the flexible tubing to prevent liquid 31 from container 32 flowing freely into a patient, due to head pressure. Free flow latch 38 does not restrict fluid flow during the normal pumping operation of volumetric pump 30, but is configured to automatically clamp proximal portion 34a of the flexible tubing when a door 78 (shown in FIGS. 2 and 3) on volumetric pump 30 is opened. While door 78 is closed, free fluid flow through volumetric pump 30 is otherwise precluded by volumetric pump 30, as explained below. The position of door 78 is sensed by a door position detector 62, producing a signal that prevents operation of volumetric pump 30 when door 78 is open. Similarly, a tubing detector 40 is interconnected to free flow latch 38, and produces a signal indicative of the presence of flexible tubing 34 within free flow latch 38; operation of volumetric pump 30 is inhibited if the signal indicates that the flexible tubing is not in place.

A balance block 42 rests against proximal portion 34a of flexible tubing 34 and serves to compensate for variations or changes in the elasticity of flexible tubing 34. The function and operation of balance block 42 are more fully explained below.

Next in the serial arrangement of components along the fluid path within volumetric pump 30 is a proximal pressure sensor 44, which operates to sense the pressure of fluid within proximal portion 34a of the flexible tubing. Proximal pressure sensor 44 produces a signal indicative of fluid pressure in this portion of flexible tubing 34 for use in monitoring the operation of the pump and to determine if proximal portion 34a has become occluded.

A key element in the operation of volumetric pump 30 is an inlet cracking valve 46, disposed immediately downstream of proximal pressure sensor 44. Inlet cracking valve 46 functions in cooperation with a plunger 48 and an outlet cracking valve 52, which are disposed sequentially downstream of the inlet cracking valve, to provide the displacement of a volumetric quantity of fluid from pumping portion 34b of the flexible tubing by volumetric pump 30 and to generally isolate the volumetric pump from variations in proximal and distal fluid pressure, due, for example, to variations in the elevation of container 32, or variations in the back pressure of fluid distal portion 34c of the flexible tubing. A flow detector 54 is interconnected with outlet cracking valve 52 and produces a signal indicating whether fluid is successfully being pumped by volumetric pump 30 into distal portion 34c. Tubing shapers 50a and 50b are disposed at each side of plunger 48 and act to rapidly reform pumping portion 34b of the flexible tubing as it refills with fluid during each pump cycle, insuring consistent volumetric refill with each pumping stroke.

A distal pressure sensor 56 produces a signal indicative of the fluid pressure within distal portion 34c of the flexible tubing, i.e., the output pressure of volumetric pump 30. The distal fluid pressure is used for monitoring the operation of volumetric pump 30 and for sensing an occlusion of flexible tubing 34.

Immediately adjacent distal pressure sensor 56 is a balance block 58. Cooperating with outlet cracking valve 52, a balance block 58 compensates for changes or variations in the stiffness or elasticity of flexible tubing 34, in a manner similar to that in which balance block 42 cooperates with inlet cracking valve 46.

An air sensor 60 is the last component along the fluid path through volumetric pump 30. Air sensor 60 detects the presence of air bubbles larger than a predefined volume in the fluid discharged from the volumetric pump, and produces a signal indicative of such air bubbles, which stops volumetric pump 30 and initiates an alarm to prevent a potentially harmful air embolism forming in the fluid being introduced into a patient through needle/catheter 36. Air sensor 60 comprises a generally conventional piezoelectric ultrasonic transmitter and receiver (not separately shown), spaced apart on opposite sides of distal portion 34c of the flexible tubing. The transmitter produces an ultrasonic signal that is transmitted through flexible tubing 34 to the receiver. Liquid present in flexible tubing 34 between the transmitter and receiver conveys the ultrasonic signal much more efficiently than does an air bubble.

The receiver produces an electronic signal in response to the level of the ultrasonic signal reaching it, the amplitude of the electronic signal indicating whether an air bubble or liquid is present in flexible tubing 34 between the transmitter and receiver. Details of air sensor 60 are not illustrated because such devices are generally well known to those of ordinary skill in this art.

Figure 2:
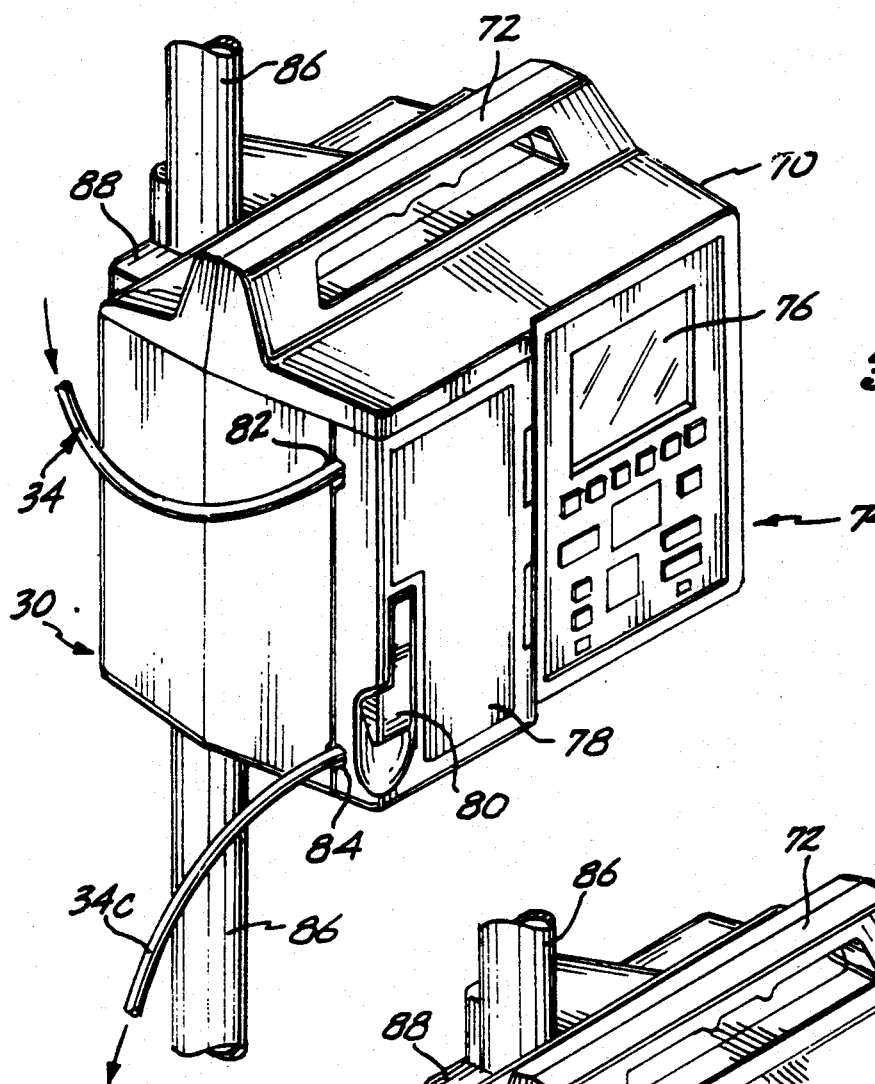
FIG. 2 is an isometric view of the volumetric pump, showing an access door that is closed and latched in place.
Figure 3:
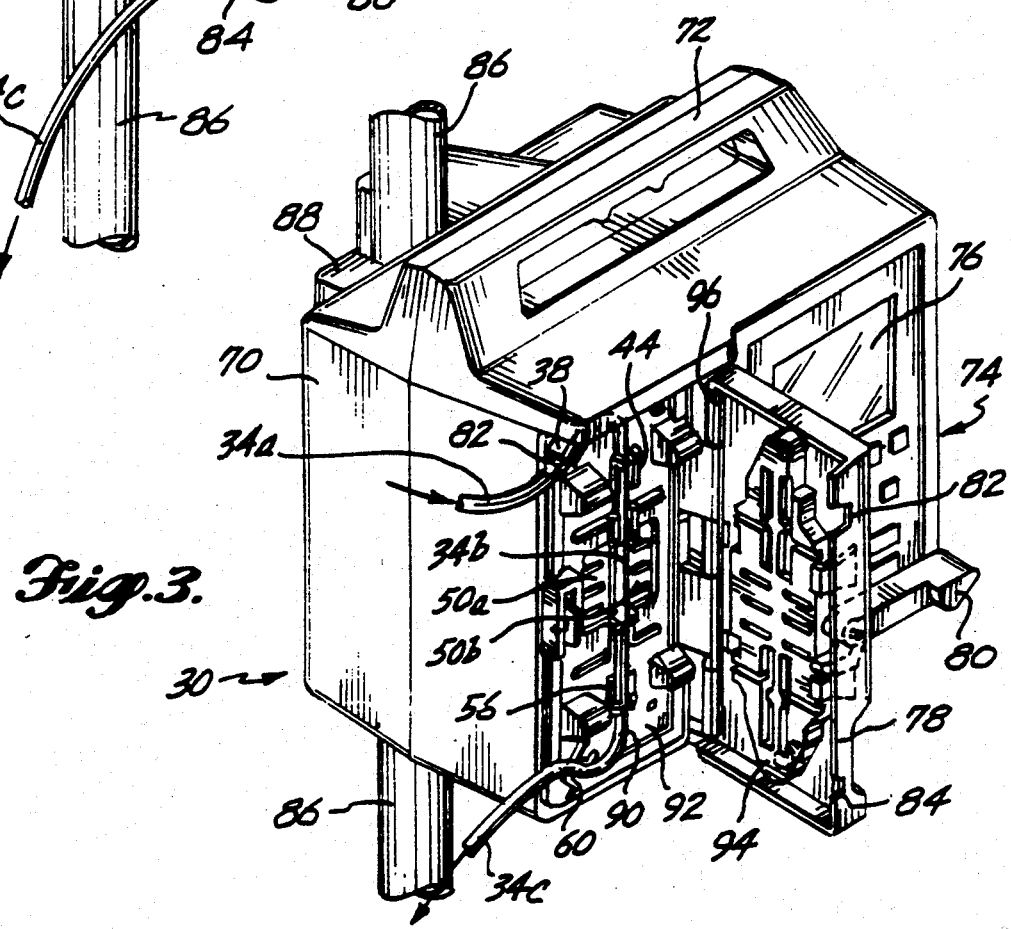
FIG. 3 is an isometric view, similar to that shown in FIG. 2, but with the access door shown in an open position, disclosing the path followed by a flexible tube through the volumetric pump.

In FIGS. 2 and 3, volumetric pump 30 is illustrated in isometric view. As shown therein, volumetric pump 30 includes a molded plastic housing 70, having a handle 72 on its upper surface to facilitate carrying the volumetric pump to a point of use. A control panel 74 and a display 76 are disposed on the right side of the front surface of volumetric pump 30, and are respectively used by an operator for entry and display of data that controls the volumetric pump.

On the back of housing 70 is formed a clamp 88, which is used to removably attach volumetric pump 30 to a post 86, for example at the bedside of a patient. Details of clamp 88 are not shown, since it is generally typical of those used with other types of medical apparatus intended for connection to vertical posts.

In FIG. 2, door 78 is shown latched closed, the appropriate disposition for use of the volumetric pump, while in FIG. 3, door 78 is shown in an open position. A latch handle 80 is pivoted upwardly so that door 78 can be swung open on a hinge 96, giving access to an inner cover 92 that defines the path followed by flexible tubing 34 through volumetric pump 30. As noted above, when door 78 is opened while flexible tubing 34 is threaded through the volumetric pump and connected to container 32, free flow latch 38 clamps the flexible tubing closed to prevent liquid 31 in container 32 from free flowing through flexible tubing 34. The mechanism that actuates free flow latch 38 when door 78 is opened is not shown since it is not particularly relevant to the present invention.

Flexible tubing 34 is angled upwardly where it passes through an entry slot 82 formed on the side of door 78, insuring that any of liquid 31 leaking from container 32 drips from a loop formed in flexible tubing 34 and does not run into volumetric pump 30. After door 78 is swung open, flexible tubing 34 is readily threaded into a channel 90 defined along the longitudinal center of inner cover 92. An exit slot 84, formed in the lower side portion of door 78, overlies distal portion 34c of the flexible tubing. A pressure plate 94 disposed on the inner surface of door 78 comes into contact with flexible tubing 34 along the length of channel 90 as door 78 is closed and latched with handle 80.

FIGS. 4, 5, and 6 show details of the interior of volumetric pump 30. Pressure plate 94 defines a reference plane or surface in respect to each of the components of volumetric pump 30 that act to compress flexible tubing 34 and is mounted so that it floats on a plurality of helical coiled springs 212. Springs 212 bias pressure plate 94 away from the inner surface of door 78. When door 78 is closed, pressure plate 94 contacts inner cover 92 at several points. Helical springs 212, which are relatively stiff, are thus slightly compressed, and therefore accommodate variations in the tolerances of door 78 and other related parts that arise during construction of volumetric pump 30. Such tolerances might otherwise affect the position of the reference plane defined by pressure plate 94.

Most of the components comprising volumetric pump 30 are mounted on a frame 100 within housing 70. For example, frame 100 includes inlet cracking valve pivot mounts 102 and outlet cracking valve pivot mounts 104, about which inlet cracking valve 46 and outlet cracking valve 52 respectively pivot.

Inlet cracking valve 46 contacts proximal portion 34a of the flexible tubing along a valve face 106a. Similarly, outlet cracking valve 52 contacts distal portion 34c of the flexible tubing along a valve face 106b. The pivotal motion of inlet cracking valve 46 and outlet cracking valve 52 respectively varies the force with which valve faces 106a and 106b contact flexible tubing 34 to control fluid flow therethrough by compressing the flexible tubing against pressure plate 94. Plunger 48 compresses pumping portion 34b of the flexible tubing against pressure plate 94 to displace fluid from within a pumping chamber defined between the inlet and outlet cracking valves 46 and 52. In part because volumetric pump 30 includes inlet and outlet cracking valves 46 and 52, it operates differently than the prior art plunger type periostaltic pumps, as will be apparent from the following disclosure.

An inlet valve arm 108 extends upwardly from valve face 106a on inlet cracking valve 46. Disposed generally above inlet cracking valve pivot mounts 102 are flat metal spring flexures 110, which connect balance block 42 to a slot 134, formed on the back side of inlet valve arm 108. Flexures 110 are snapped within slot 134 and flex to enable inlet valve arm 108 to pivot valve face 106a away from pressure plate 94 through a greater angle that would otherwise be possible, without closing off fluid flow through flexible tubing 34 due to compression of the flexible tubing by balance block 42. Inlet cracking valve pivot mounts 102 are connected to downwardly depending pivot arms 136 on inlet cracking valve 46, at each side of flexible tubing 34, and are centered between balance block 42 and valve face 106a. The stiffness of flexible tubing 34 acts on balance block 42 and flexures 110, and the balance force developed as a function of this stiffness (or lack of elasticity) tends to pivot inlet valve face 106a against pressure plate 94, thereby increasing the force exerted by that part of inlet cracking valve 46 to compress the flexible tubing. The stiffness of flexible tubing 34 also resists compression by inlet valve face 106a to a similar extent. Accordingly, variations in the elasticity of flexible tubing 34 that affect the force required for inlet valve face 106a to compress the tubing are automatically compensated for by balance block 42.

Inlet cracking valve 46 operates in three distinct modes, the force applied by valve face 106a to compress flexible tubing 34 being substantially different in each mode. Two different spring-bias forces act on inlet valve arm 108. A fluid flow control force is applied to inlet valve arm 108 by a flat metal spring cracking flexure 112, acting against a knob 114, which is disposed at one end of inlet valve arm 108. The additional force necessary to compress flexible tubing 34 sufficiently to completely close off fluid flow past inlet cracking valve 46 is supplied by a flat metal spring closure flexure 120. Closure flexure 120 acts upon a side arm 116, disposed on one side of inlet valve arm 108. The combined force provided by cracking flexure 112 and closure flexure 120 (in addition to the balance force provided by balance block 42) pivots inlet cracking valve 46 about a pivot axis extending through inlet cracking valve pivot mounts 102, to completely block fluid flow through flexible tubing 34.

An inlet valve cam follower 122 selectively determines whether cracking flexure 112 and closure flexure 120 apply force against inlet valve arm 108 and thus determines the three modes in which inlet cracking valve 42 operates. Inlet valve cam follower 122 includes a roller 124 rotatably mounted in a hood 126, which is attached via an inlet follower flexure 128 to a plurality of blocks 130. Blocks 130 are also used in mounting cracking flexure 112 and closure flexure 120 to a bracket 135 and to provide appropriate spacing between these flexures and bracket 135. Bolts 132 connect the ends of each of these flexures to bracket 135, which comprises a portion of frame 100.

Roller 124 rolls along an inlet valve cam track 140, disposed on a rotating cam assembly 142. Cam assembly 142 turns on a camshaft 144, which at each of its ends is mounted to frame 100 in bearings 220 (see FIGS. 5 and 6). A motor shaft 148 extends downwardly from a motor 146, and a helical gear 224 on motor shaft 148 drivingly engages gear teeth 222, which are formed on one end of cam assembly 142, causing the cam assembly to rotate in a clockwise direction, as viewed in FIG. 4. The radial distance between camshaft 144 and the point where roller 124 contacts the surface of inlet valve cam track 140 varies as cam assembly 142 rotates, moving inlet valve cam follower 122 radially back and forth so as to control the forces applied to inlet valve arm 108. Specifically, as hood 126 is forced radially back against closure flexure 120, it lifts the closure flexure away from side arm 116, eliminating the force normally exerted by the by valve face 106a against flexible tubing 34. In this configuration, inlet cracking valve 46 is in a "cracking mode."

As hood 126 moves further radially outward, closure flexure 120 contacts a "V-shaped" side arm 118 that is formed on the side of inlet valve arm 108, causing inlet valve arm 108 to pivot valve face 106a away from pressure plate 94. In this configuration, inlet cracking valve 46 is in an open mode, wherein liquid 31 freely flows from container 32 through proximal portion 34a of the flexible tubing and into pumping portion 34b. Flexures 110 bend as valve face 106a pivots away from pressure plate 94, so that balance block 42 does not close off fluid flow through proximal portion 34a of the flexible tubing.

When both closure flexure 120 and cracking flexure 112 are allowed to act on inlet valve arm 108, valve face 106a compresses flexible tubing 34 against pressure plate 94 sufficiently to completely block fluid flow through the flexible tubing. In this configuration, inlet cracking valve 46 is in a "closed mode."

An outlet valve cam track 150 is disposed between inlet valve cam track 140 and a plunger cam track 152. Plunger cam track 152 provides a surface at varying radii about camshaft 144 for actuating plunger 48 to compress pumping portion 34b of the flexible tubing against pressure plate 94. A roller 154 is rotatably mounted on a base 156 of olunger 48, and is thus disposed to roll along plunger cam track 152. Also mounted on base 156, at opposite sides of roller 154, are tubing shaper rollers 160. The disposition of tubing shaper rollers 160 is more clearly shown in FIGS. 5 and 6, and their operation in respect to shaping flexible tubing 34 is disclosed in detail below.

As shown using hidden lines in FIG. 4, the back side of cam assembly 142 includes a torque compensation track 170. A conically-shaped torque compensation roller 172 rolls along torque compensation track 170, applying a rotational torque to cam assembly 142 that compensates for an opposite torque resulting from rapid changes in the shape of inlet valve cam track 140, outlet valve cam track 150, and plunger cam track 152. Torque compensation roller 172 is mounted on a flat metal spring torque compensation flexure 174 that applies a biasing force to cam assembly 142.

Like inlet cracking valve 46, outlet cracking valve 52 has a generally "Y-shaped" configuration and includes an outlet valve arm 180, which is connected to outlet valve face 106b and to balance block 58. On opposite sides of flexible tubing 34, pivot arms 136 extend downwardly, connecting to outlet cracking valve pivot mounts 104 on frame 100. Balance block 58 rest on distal portion 34c of the flexible tubing and develops a force proportional to the stiffness (or lack of elasticity) of flexible tubing 34, which tends to increase the compression force applied against flexible tubing 34 by outlet valve face 106b to compensate or balance the resistance to compression caused by the stiffness (or lack of elasticity) of the flexible tubing. Just as balance block 42 compensates for changes or variations in elasticity of the flexible tubing in respect to inlet cracking valve 46, balance block 58 compensates for such changes and variations in respect to outlet cracking valve 52. However, since outlet cracking valve 52 is never pivoted to an open mode like inlet cracking valve 46, balance block 58 is integrally attached to outlet valve arm 180. Flexures 110 are not required, since the extent of pivotal rotation of outlet cracking valve 52 is substantially more limited than for inlet cracking valve 46. At all times, even when volumetric pump 30 is not pumping fluid, either inlet cracking valve 46 or outlet cracking valve 52 is in its closed mode, preventing liquid 31 from free flowing through flexible tubing 34.

As shown in FIG. 4, outlet cracking valve 52 is in its closed mode, compressing flexible tubing 34 against pressure plate 94 sufficiently to block fluid flow therethrough. In this configuration, a flat metal spring cracking flexure 182 applies force against a knob 184 on the top of outlet valve arm 180. In addition, a flat metal spring closure flexure 188 applies a biasing force against a side arm 186 that extends outwardly from the side of outlet valve arm 180.

An outlet valve cam follower 190 includes a roller 192, which rolls along outlet valve cam track 150. Roller 192 is rotatably mounted within a hood 194, which is connected to a flat metal spring follower flexure 196. Follower flexure 196 spring biases roller 192 into contact with outlet valve cam track 150. The lower ends of follower flexure 196, cracking flexure 182, and closure flexure 188 are all secured at blocks 130 to bracket 135 by bolts 132, just as the corresponding elements are in respect to inlet cracking valve 46. As outlet valve cam follower 190 follows outlet valve cam track 150, hood 194 periodically contacts closure flexure 188, lifting it away from side arm 186 so that the flow control force provided by cracking flexure 182, added to the balance force developed by balance block 58, is transmitted to valve face 106b, thereby compressing flexible tubing 34 against pressure plate 94 with a cracking force. In this configuration, outlet cracking valve 52 is in its cracking mode.

As plunger 48 compresses pumping portion 34b of the flexible tubing against pressure plate 94, the pressure developed by liquid trapped between inlet cracking valve 46, which is closed, and outlet cracking valve 52 acts on valve face 106b, in opposition to the cracking force produced by cracking flexure 182 and balance block 58. As the force developed by the fluid pressure reaches a predetermined level sufficient to cause outlet cracking valve 52 to pivot open slightly, liquid 31 flows past the outlet cracking valve from pumping portion 34b of the flexible tubing. Liquid 31 is thus delivered by volumetric pump 30 at a predefined cracking pressure.

A strain gauge 198 is mounted to cracking flexure 182. Strain gauge 198 develops an output signal corresponding to the stress developed in cracking flexure 182, therefore indicating the pivotal motion of outlet valve arm 180 as it rotates to allow fluid flow past outlet cracking valve 52. Accordingly, strain gauge 198 comprises flow detector 54 for determining whether fluid is being pumped through distal portion 34c of the flexible tubing as a result of displacement by plunger 48. If pumping portion 34b of the flexible tubing contains a relatively large proportion of air or other compressible gaseous fluid, plunger 48 cannot develop sufficient fluid pressure to overcome the cracking force exerted by cracking flexure 182 and balance block 58. As a result, strain gauge 198 fails to detect the pivotal motion of outlet valve arm 180, indicating that fluid flow past outlet cracking valve 52 has not occurred during a pumping stroke of plunger 48. Accordingly, the signal from strain gauge 198 can be used to detect whether container 32 has run dry or whether flow of liquid 31 into volumetric pump 30 has otherwise been interrupted. The signal produced by strain gauge 198 is simply a "go/no-go" signal as opposed to a signal that is accurately proportional to the movement of outlet valve arm 180. This go/no-go signal is used to stop volumetric pump 30 and initiate an alarm when the expected fluid flow is not obtained, thereby alerting medical personnel of the problem so that it can be corrected.

Instead of strain gauge 198, various other types of motion sensors may be used to produce a signal indicative of the pivotal motion of outlet valve arm 180. For example, outlet valve arm 180 can be connected to a linear variable displacement transformer (LVDT) that uses motion to produce a signal corresponding to a relative change in the magnetic coupling between two electromagnetic coils, or may comprise a variable capacitor that changes capacitance value as outlet valve arm 180 pivots. Similarly, a Hall sensor or optical sensor can be used to detect pivotal motion of outlet valve arm 180, and thus may serve as alternative types of flow detectors.

Proximal pressure sensor 44 comprises a block 204, which is spring biased into contact with proximal portion 34a of the flexible tubing, and is disposed between inlet cracking valve 46 and balance block 42. A spring-bias force for proximal pressure sensor 44 is provided by two pairs of longitudinally-extending flexures 202, disposed on each side of plunger 48. Flexures 202 are connected to support plates 266 on frame 100 by fasteners 206 at about the midpoint of the flexures. One of the four flexures 202 connecting block 204 to support plates 266 includes a strain gauge 200, which responds to stress developed in that flexure 202 as a function of fluid pressure within proximal portion 34a of the flexible tubing. As the fluid pressure increases within this portion of flexible tubing 34, flexures 202 connected to block 204 experience increased stress, producing a corresponding change in the output signal from strain gauge 200.

Similarly, distal pressure sensor 56 comprises a block 210, which is connected to the other ends of flexures 202. A strain gauge 208 is disposed on one of the four flexures, intermediate block 210 and one of the support plates 266. Strain gauge 208 produces a signal corresponding to the fluid pressure within distal portion 34c of the flexible tubing, based upon stress developed in flexures 202 as a result of that pressure. Distal pressure sensor 56 can be used to determine if distal portion 34c of the flexible tubing has been kinked, interrupting fluid flow through flexible tubing 34, for example, as might occur if a patient rolled over onto flexible tubing 34. Such a condition causes a notable increase in the distal fluid pressure that triggers an alarm and shuts off volumetric pump 30.

In FIGS. 5, 6, and 7, details of tubing shapers 50a and 50b are disclosed. Since it is preferable to use relatively low cost PVC tubing in connection with volumetric pump 30, tubing shapers 50a and 50b are provided to ensure consistent operation and volumetric capacity of pumping portion 34b of the flexible tubing throughout the entire operating range of volumetric pump 30. At relatively high pumping rates, PVC tubing does not fully recover to its normal round uncompressed shape from a compressed condition rapidly enough to fill completely with fluid. Accordingly, the volumetric displacement of fluid within the PVC tubing that occurs with each pumping stroke is less than desired. To avoid this problem, tubing shapers 50a and 50b force pumping portion 34b of the flexible tubing to recover rapidly to its maximum volumetric capacity, i.e., to open sufficiently so that the desired amount of liquid 31 fills the pumping chamber defined by pumping portion 34b of the flexible tubing.

Each tubing shaper 50a and 50b comprises an angled arm 234, terminating at one end in a longitudinally-extending jaw 236. Arms 234 are attached to frame 100 at pivot mounts 230, about which arms 234 rotate as tubing shaper rollers 160 roll along inner surfaces 232 of arms 234. Thus, the reciprocating up-and-down motion of plunger 48 along its reciprocation axis inherently acts on tubing shaper rollers 160 in "lock-step", causing jaws 236 to pinch pumping portion 34b of the flexible tubing at the proper time, thereby reforming flexible tubing 34 into the required pumping volume or capacity as plunger 48 lifts away from pressure plate 94.

In FIG. 5, tubing shapers 50a and 50b are shown moving in opposite directions, away from pumping portion 34b of the flexible tubing as plunger 48 descends to compress flexible tubing 34, displacing fluid from pumping portion 34b. However, in FIG. 6, plunger 48 is shown moving upwardly away from pressure plate 94, acting on tubing shaper rollers 160 to force opposing jaws 236 to swing inwardly toward each other in order to reshape pumping portion 34b of the flexible tubing so that it achieves its desired volumetric capacity.

To further enhance the repeatability and consistency of the volumetric capacity defined in pumping portion 34b of the flexible tubing, plunger cam track 152 is sized and shaped so that plunger 48 never completely compresses pumping portion 34b of the flexible tubing, even at the lower-most point of the plunger's reciprocal stroke. In addition, at the top of its reciprocal stroke, plunger 48 remains in contact with pumping portion 34b of the flexible tubing. The range of diametrical compression of flexible tubing 34 is from about 15% at the top of the pumping stroke to about 85% at the bottom of the pumping stroke of plunger 48. Since flexible tubing 34 need not recover to a fully uncompressed condition, i.e., to a perfect circular cross section, changes in the elasticity of flexible tubing 34 due to continued use and repeated compression have much less effect on the volumetric capacity of pumping portion 34b of the flexible tubing than would otherwise occur.

In order to calibrate tubing shapers 50a and 50b so that their range of motion corresponds to that required to achieve proper reshaping of pumping portion 34b of the flexible tubing, a wedge-shaped slot 240 is provided in the upper outer portion of arms 234. To adjust the angle between the upper and lower portions of each arm 234, a wedge-shaped insert 238 is driven into wedge-shaped slot 240, deflecting the upper portion of arm 234 through an angle, as indicated by reference numeral 242. Angle 242 is determined by use of an appropriate calibration jig (not shown) during manufacture of tubing shapers 50a and 50b, or during assembly of these components in volumetric pump 30.

Details of inlet cracking valve 46 are shown in FIG. 8, and details of outlet cracking valve 52 are shown in FIG. 9. In these drawings, it is apparent that downwardly depending pivot arms 136 straddle flexible tubing 34, and are spaced apart sufficiently so that blocks 204 and 210 of proximal pressure sensor 44 and distal pressure sensor 56 can fit therebetween. FIG. 8 more clearly illustrates side arm 116 and V-shaped side arm 118 at the top of inlet valve arm 108. In FIG. 9, the specific disposition of side arm 186 in respect to outlet valve cam follower 190, closure flexure 188, and cracking flexure 182 is also more clearly shown.

One of the advantages of using flat metal spring flexures, i.e., cracking flexure 112 and closure flexure 120, for biasing inlet valve arm 108 is that the force provided by each of these flexures is much more readily controlled than is typically the case with other types of spring assemblies. For example, by trimming the shape of these flexures or selecting flexures of a different thickness, the spring force they produce (i.e., their spring constant, K) can be readily modified and consistently controlled. The same advantages apply to the other flexures used in volumetric pump 30, such as inlet follower flexure 128 and balance block flexures 110. Accordingly, the cracking pressure and other characteristics of volumetric pump 30 can be precisely determined.

Figure 15:
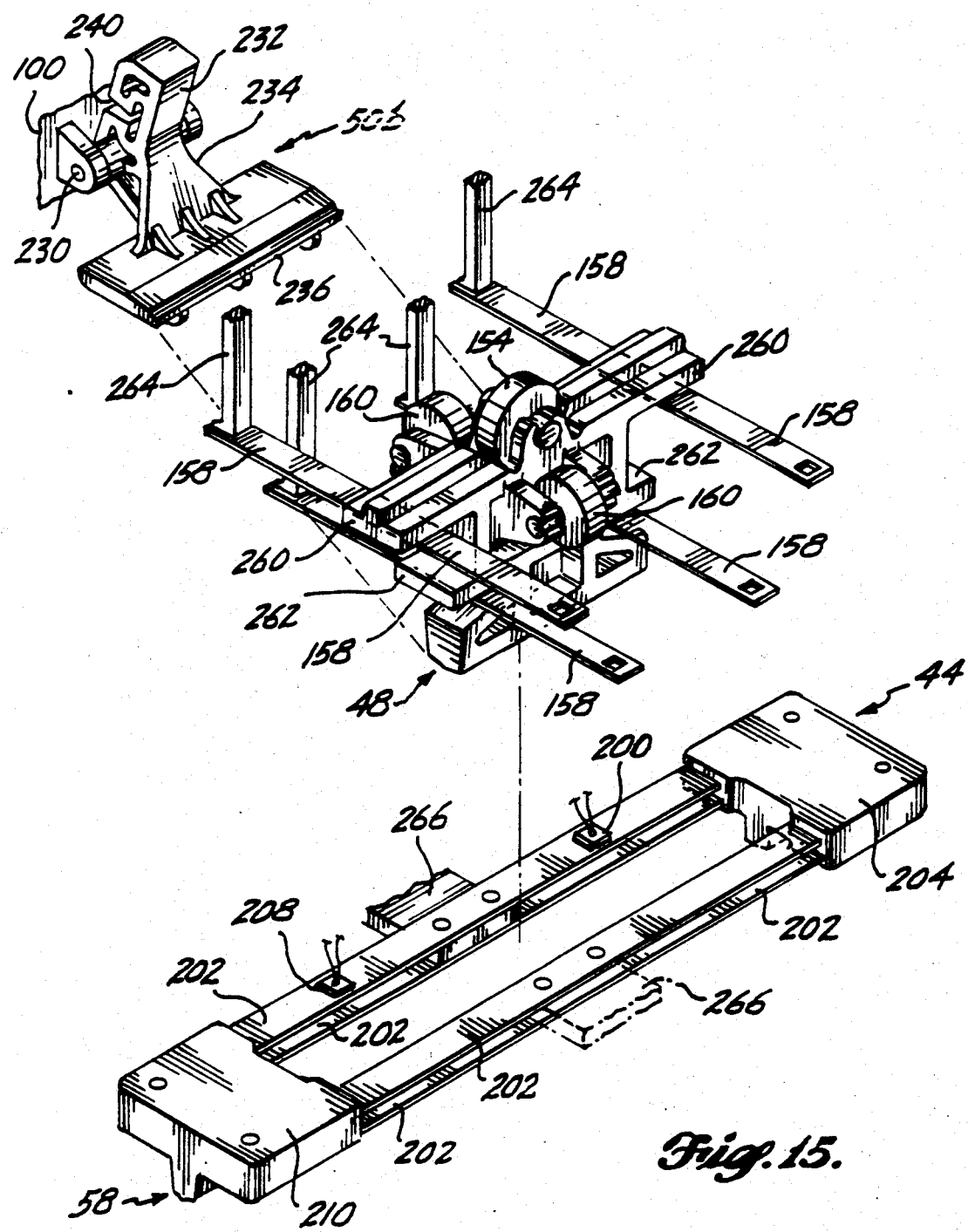
FIG. 15 is an exploded view isometrically illustrating one of the tube reshapers, the plunger and support flexures, and pressure sensors used in the volumetric pump.
Figure 16:
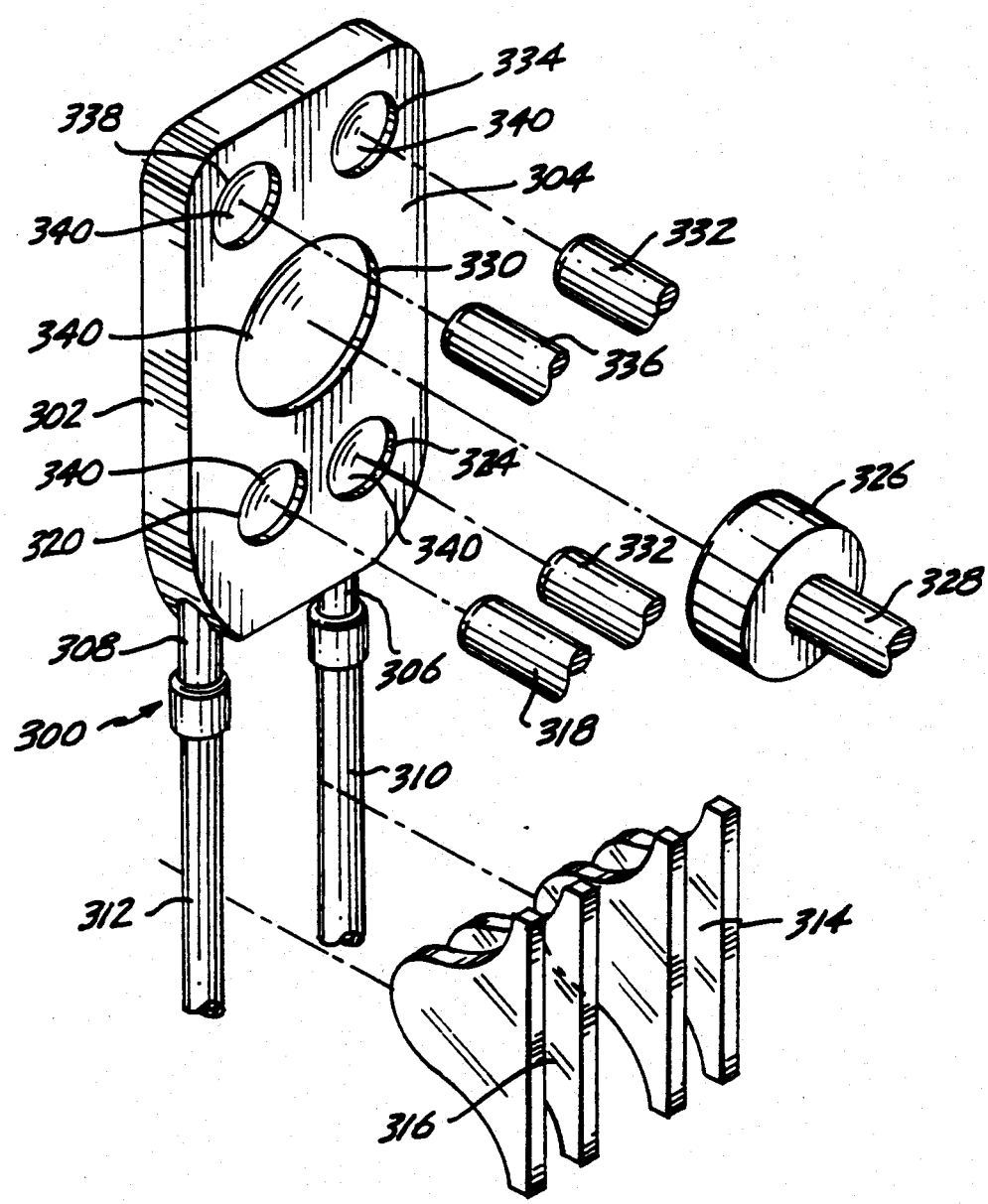
FIG. 16 is an isometric view of a cassette used with a different embodiment of the volumetric pump.

The consistent volumetric displacement of fluid developed by volumetric pump 30 is in part due to the free floating suspension of plunger 48 provided by other flexure components. As shown in FIG. 15, plunger 48 is supported by two pairs of transversely-extending flat metal spring flexures 158. The ends of flexures 158 are mounted to frame 100 via posts 264, only a few of which are shown in FIG. 15 for clarity. The two flexures 158 in each pair of flexures are generally parallel to each other and are connected to plunger 48 at spaced-apart points, thereby ensuring that plunger 48 is free to move along a reciprocation axis, in a direction transverse to the longitudinal axis of flexible tubing 34, but is constrained by flexures 158 to resist twisting and lateral displacement.

Plunger base 156 includes two long arms 260 extending longitudinally on each side of roller 154, and two shorter arms 262, also extending longitudinally, but disposed below tubing shaper rollers 160. One pair of flexures 158 are connected to long arms 260, and the other pair of flexures 158 are connected to shorter arms 262. By mounting plunger 48 to flexures 158 at these two different elevational positions along its reciprocation axis, and by providing different spacing between the flexures attached to long arms 260 as compared to the spacing between the flexures 158 attached to shorter arms 262, substantial rigidity is obtained in respect to possible movement by plunger 48 in all directions, except up and down along its reciprocation axis. Each flexure 158 readily bends elastically about an axis that extends across its flat surface, transverse to its longitudinal axis, but is quite stiff in resisting bending about an orthogonal axis that is normal to its flat surface. Flexures 158 are also relatively stiff and unyielding in respect to longitudinal tension or compression forces. These properties, coupled with the arrangement of flexures 158 used to support plunger 48 provide the resistance to motion of the plunger along all but the reciprocation axis noted above. Flexures 158 also provide a biasing force directed along the reciprocation axis that maintains roller 154 in contact with plunger cam track 152.

Figure 14:
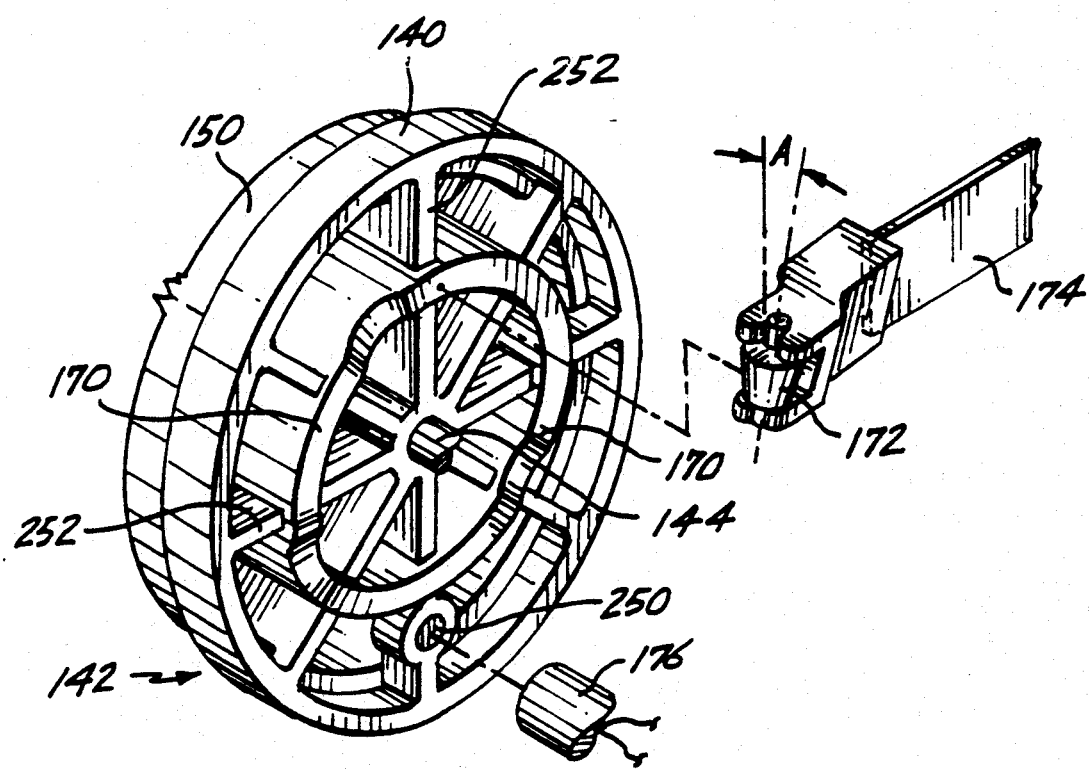
FIG. 14 is an isometric view of a portion of the cam assembly, illustrating a torque compensation track, a torque compensation follower and roller, and a cam assembly position sensor.

FIG. 14 illustrates details of torque compensation track 170, which is disposed on the back side of cam assembly 142. The profile or displacement of torque compensation track 170 varies in a direction generally parallel to camshaft 144, and compensates for torque developed on the other three cam tracks 140, 150, and 152 defined on cam assembly 142 as the corresponding cam followers travel along rapidly changing radial pitches. A rapid radial change in the profile of one of these cam tracks develops an angular torque component tending to rotate cam assembly 142, which can overdrive motor 146 beyond its desired speed. To compensate and prevent such variation in the speed of cam assembly 142, torque compensation track 170 is profiled to develop an opposing torque that acts on cam assembly 142. Torque compensation roller 172 has a conical shape and is mounted on torque compensation flexure 174 at an angle "A" corresponding to the cone angle of the roller to accommodate the different rates of linear travel of torque compensation roller 172 along the radially inner and outer edge of torque compensation track 170. A round torque compensation roller would scrub and wear if used in place of conical torque compensation roller 172.

Figure 11:
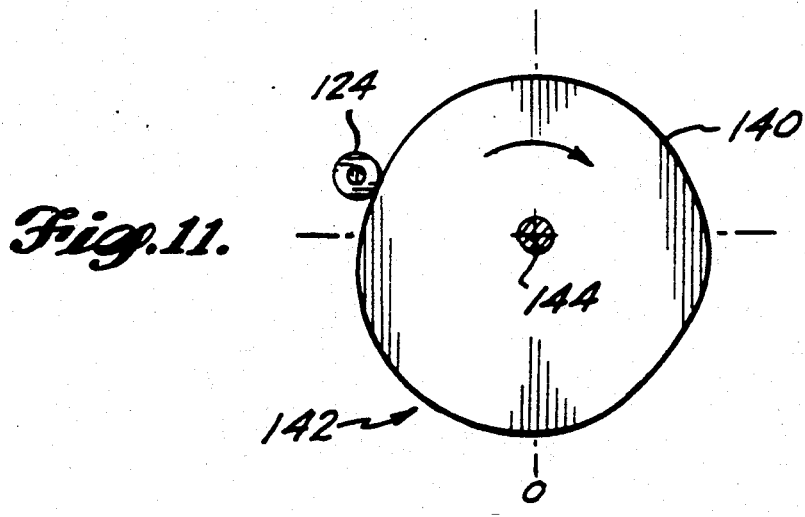
FIG. 11 illustrates a profile of the inlet cracking valve cam track.
Figure 12:
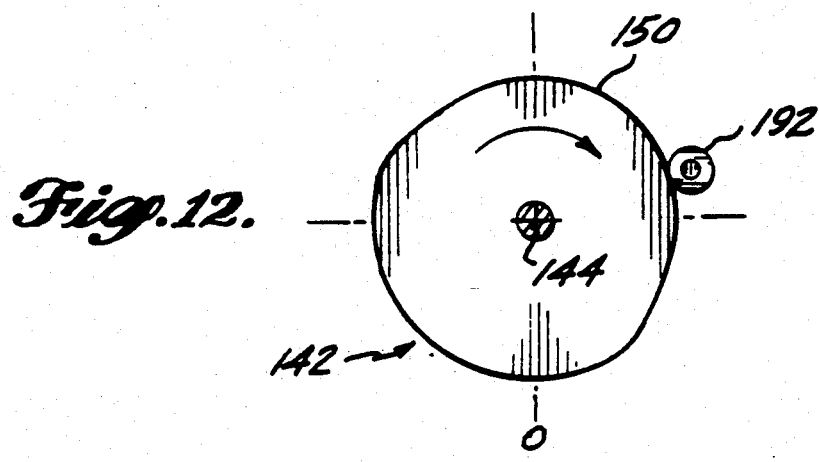
FIG. 12 illustrates a profile of the outlet cracking valve cam track.
Figure 13:
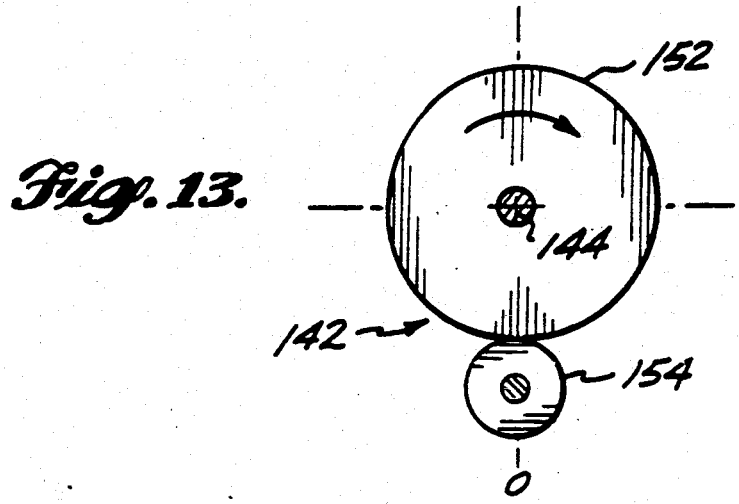
FIG. 13 illustrates a profile of the plunger cam track.

As also shown in FIG. 14, a Hall sensor 176 is positioned to detect a home position of cam assembly 142 at each of its rotations, as a magnet 250 disposed in cam assembly 142 passes Hall sensor 176. FIGS. 11, 12, and 13 illustrate the profile of inlet valve cam track 140, outlet valve cam track 150, and plunger cam track 152 in respect to the home position, which is indicated at the bottom of each of the cam track profiles at 0° rotation. Each pumping cycle of volumetric pump 30 corresponds to 360° of rotation of cam assembly 142 from the home position shown in FIGS. 11, 12, and 13.

The operation of volumetric pump 30 can be readily understood by reference to FIGS. 10A, 10B, and 10C. In these Figures, a less detailed, longitudinal schematic view of volumetric pump 30 is shown from the opposite side, as compared to FIG. 4. Thus, in FIGS. 10A–10C, fluid enters volumetric pump 30 from the left side, where proximal portion 34a of the flexible tubing is disposed, and exits toward the right, into distal portion 34c of the flexible tubing. The advantage of viewing the operation of volumetric pump 30 from this perspective is that the relative positions of cracking flexures 112 and 182, closure flexures 120 and 188, and cam followers 122 and 190 can readily be observed in respect to valve arms 108 and 180.

In FIG. 10A, volumetric pump 30 is shown with inlet cracking valve 46 in its open mode, wherein valve face 106a is lifted away from pressure plate 94 to permit fluid flow from container 32 into pumping portion 34b of the flexible tubing. This view corresponds to a fill segment of the pumping cycle. To achieve this configuration, cam assembly 142 rotates to a position where roller 124 contacts inlet valve cam track 140 at its maximum radial distance from camshaft 144. Inlet valve cam follower 122 is forced radially outward (to the left) sufficiently so that hood 126 contacts closure flexure 120, forcing it away from side arm 116 and into contact with V-shaped side arm 118, thereby pivoting inlet cracking valve 46 counterclockwise around pivot mounts 102. In this rotational position, roller 154 contacts plunger cam track 152 at its minimum radial profile, permitting plunger 48 to move reciprocally to its uppermost position, wherein the plunger maintains pumping portion 34b of the flexible tubing at approximately a 15% diametrical compression. Further, outlet valve cam follower 190 is disposed at a minimum radial profile portion of outlet valve cam track 150, enabling closure flexure 188 to act on side arm 186. The combined force of closure flexure 188 and cracking flexure 182 pivot outlet valve arm 180 counterclockwise around pivot mounts 104, bringing outlet valve face 106b into compressive contact with flexible tubing 34 with enough force to completely close off fluid flow through the flexible tubing.

In FIG. 10B, cam assembly 142 has rotated into a pumpback-pressurization segment of the pumping cycle. During the pumpback-pressurization segment, outlet cracking valve 52 remains completely closed, as shown in FIG. 10A, while inlet cracking valve 46 is in its cracking mode. In the cracking mode, roller 124 contacts inlet valve cam track 140 at a point that defines an intermediate radius about camshaft 144. In this position, hood 126 of inlet valve cam follower 122 lifts closure flexure 120 away from side arm 116 so that only cracking flexure 112 acts on inlet valve arm 108, producing most of the desired cracking force. As described above, the rest of the cracking force is developed by balance block 42, which provides a balance force that compensates for variations and changes in the stiffness or elasticity of flexible tubing 34 that might otherwise vary the desired cracking force.

During the pumpback-pressurization segment of the pumping cycle, plunger 48 descends from the top of the intake stroke, as shown in FIG. 10A, to the top of the pumping stroke, wherein pumping portion 34b of the flexible tubing is diametrically compressed by approximately 40%. As plunger 48 descends from the top of the intake stroke to the top of the pumping stroke, fluid pressure inside pumping portion 34b of the flexible tubing increases until it reaches a cracking pressure, at which point the force developed by the fluid pressure acting upon the surface of valve face 106a is sufficient to overcome the cracking force, thereby opening inlet cracking valve 46 and allowing retrograde fluid flow through it from the pumping portion, back toward container 32. During the pumpback-pressurization segment of the pumping cycle, excess fluid within pumping portion 34b of the flexible tubing is thus forced back into proximal portion 34a of the flexible tubing. As the pumping segment of the pump cycle begins, only a predefined volume of fluid is contained within pumping portion 34b of the flexible tubing.

Finally, during a pumping segment of the pumping cycle that is represented in FIG. 10C, cam assembly 142 rotates to a point wherein roller 124 contacts inlet valve cam track 140 at a minimum radius about camshaft 144, such that inlet cracking valve cam follower 122 is no longer in contact with closure flexure 120. Under this condition, both cracking flexure 112 and closure flexure 120 act upon inlet valve arm 108, producing a total force that causes valve face 106a to compress flexible tubing 34 against pressure plate 94, thereby completely blocking fluid flow past inlet cracking valve 46 in either direction.

Meanwhile, outlet cracking valve 52 switches to its cracking mode, as hood 194 on the outlet valve cam follower 190 lifts closure flexure 188 away from side arm 186 so that the closure flexure no longer applies a force against outlet valve arm 180. In this configuration, cracking flexure 182 provides most of the predefined cracking force acting to compress flexible tubing 34 against pressure plate 94 at outlet valve face 106b. Balance block 58 provides the remainder of the predefined cracking force, compensating for variations in the stiffness or elasticity of flexible tubing 34, and thereby preventing such variations from affecting the desired predefined cracking force. Plunger 48 continues to descend, further compressing pumping portion 34b of the flexible tubing. Fluid pressure within the pumping portion is already at the desired cracking pressure from the pumpback-pressurization segment of the pumping cycle, and this cracking pressure acts on the surface of valve face 106b, immediately creating a force that exceeds the cracking force of outlet cracking valve 52. The cracking pressure of the fluid (liquid 31) causes outlet cracking valve 52 to pivot clockwise about pivot mounts 104 sufficiently to enable fluid flow into distal portion 34c of the flexible tubing. Plunger 48 continues to descend until it reaches approximately 85% diametrical compression of pumping portion 34b of the flexible tubing. At this point, a predefined volume of fluid, e.g., 100 microliters, at a predefined cracking pressure has been displaced from volumetric pump 30 into distal portion 34c of the flexible tubing.

From the preceding explanation, it should be apparent that each pumping cycle of volumetric pump 30 includes three distinct segments: (1) a fill segment during which a pumping chamber defined between inlet cracking valve 46 and outlet cracking valve 52, i.e., the volume within pumping portion 34b of the flexible tubing, fills with fluid; (2) a pumpback-pressurization segment, wherein excess fluid within the pumping portion of the flexible tubing is forced back into proximal portion 34a of the flexible tubing, toward container 32 as the fluid is pressurized to the cracking pressure; and (3) a pumping segment, wherein fluid within the pumping portion of the flexible tubing at the cracking pressure is forced from volumetric pump 30 into distal portion 34c of the flexible tubing. Each of these pumping cycle segments is separated from the next by a short dwell period. In the preferred embodiment of volumetric pump 30, each pumping cycle, i.e., each revolution of cam assembly 142, corresponds to 24 revolutions of motor shaft 148. Thus, each revolution of motor shaft 148 corresponds to a 15° rotation of cam assembly 142. Table I lists the revolutions of motor shaft 148 and degrees of rotation of cam assembly 142 for each portion of the pumping cycle.

TABLE I

| Pumping Cycle Segment | Deg. of Rotation | Motor Shaft Revs.* |
|---|---|---|
| Pumping | 135 | 9 |
| Dwell | 25 | 2 |
| Fill (intake) | 110 | 7 |

TABLE I-continued

| Pumping Cycle Segment | Deg. of Rotation | Motor Shaft Revs.* |
|---|---|---|
| Dwell | 20 | 1 |
| Pumpback-Pressuriz. | 45 | 3 |
| Dwell | 25 | 2 |

*In Table I, the revolutions of motor shaft 148 corresponding to degrees rotation of cam assembly 142 are approximate, having been rounded to integer numbers.

Motor 146 includes a Hall sensor (not shown) that is used to monitor the rotational position of motor shaft 148. Also, in the preferred form of volumetric pump 30, motor 146 incorporates an optical encoder (not shown) providing 100 increments of rotational resolution, one increment of which corresponds to a home position of motor shaft 148. However, since each rotation of cam assembly 142 corresponds to 24 revolutions of motor shaft 148, Hall sensor 176, which responds to magnet 250 on the back of cam assembly 142, is used to roughly define the home position of the camshaft, subject to the finer resolution for home position determined by either the Hall sensor or optical encoder incorporated in motor 146. Hall sensor 176 need only define home position within ±7.5°, since true home position (referred to as "home/home" position) is determined internally within motor 146.

Figure 22:
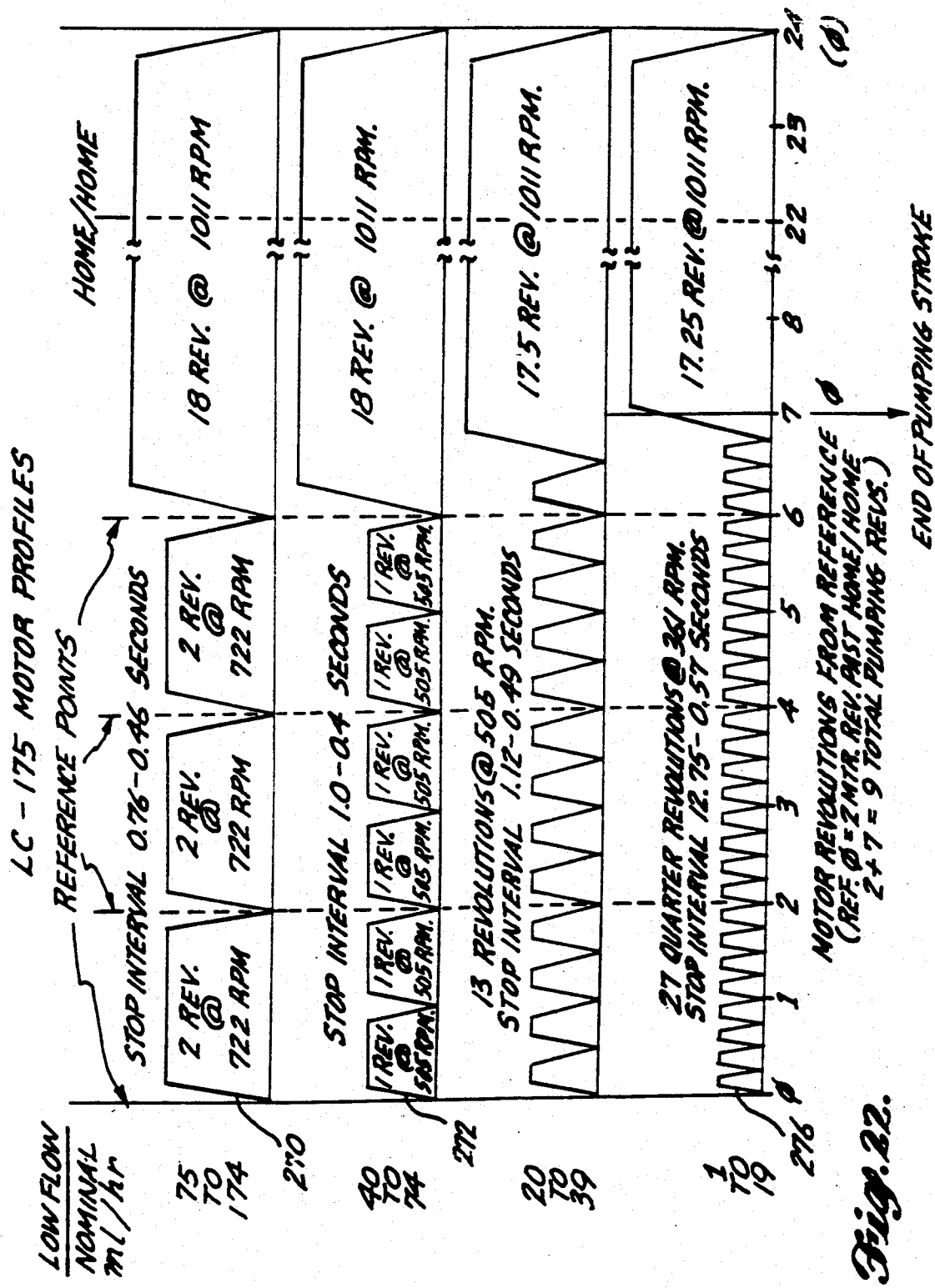
FIG. 22 is a timing chart indicating the timing motor shaft revolutions and rpm for low flow ranges of the volumetric pump.

Volumetric pump 30, in its preferred form, is capable of pumping fluid at rates from 1-999 ml/hr. Fluid flow rates in the range 175-999 ml/hr are achieved by varying the rotational rate of motor 146. In the preferred embodiment, motor 146 comprises a DC brushless motor capable of speeds over 4,000 rpm; however, other types of motors may also be used. To achieve flow rates between 1 and 174 ml/hr, motor 146 is operated in one of four separate ranges, identified in FIG. 22 by reference numerals 270, 272, 274, and 276. In each of these ranges, motor 146 is stopped during the pumping segment of the pumping cycle for a different number of intervals, and for varying amounts of time at each interval. For example, to achieve 174 ml/hr as shown in range 270, motor 146 operates at 722 rpm during the pumping segment, and stops for 0.46 second intervals between each of three 2-revolution portions of the pumping segment. To achieve 75 ml/hr in the same range, motor 146 again runs at the same speed, but stops for 0.76 second intervals between each of the 2-revolution portions of the pumping segment. During each of the low flow rate ranges 270-276, the remainder of the pumping cycle is completed at 1,011 rpm, including two revolutions past the home position, which carry the pumping cycle into the next pumping segment. On FIG. 22, the dashed line identifying home/home (in the upper right corner) refers to the true home position for both motor 146 and for cam assembly 142, as described above.

Figure 23:
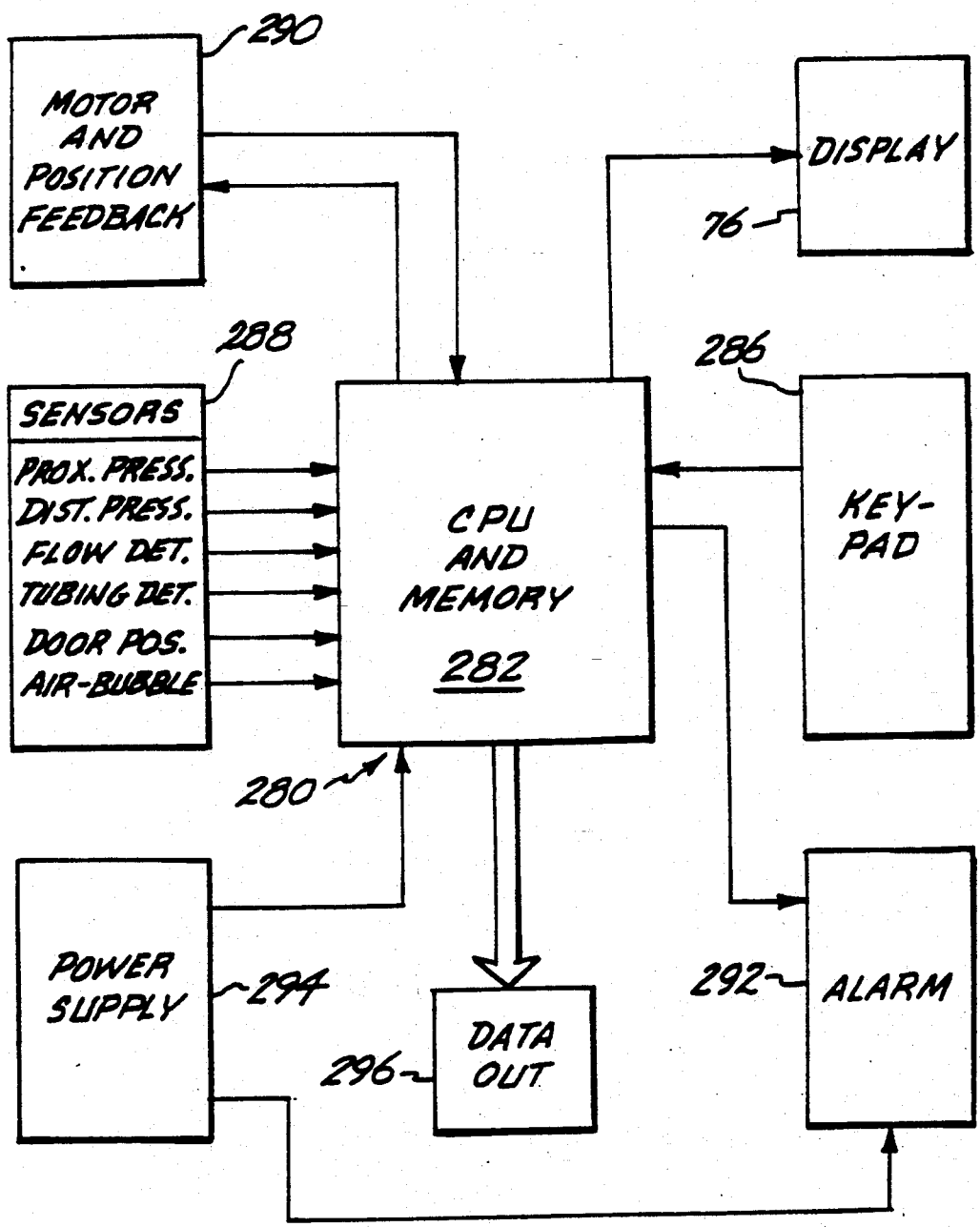
FIG. 23 is a schematic block diagram illustrating a volumetric pump controller.

Turning now to FIG. 23, a controller for volumetric pump 30 is shown generally at reference numeral 280. Controller 280 includes a microprocessor CPU and memory block 282 in which software algorithms that control volumetric pump 30 are implemented in response to input control data provided by an operator on a keypad 286. For example, an operator might enter specific times during which a prescribed volume of liquid 31 should be administered intravenously to a patient at a prescribed flow rate by volumetric pump 30. The control data entered via keypad 286 are shown on display 76.

In accord with the control data entry provided on keypad 286, CPU and memory block 282 actuates the motor at the required time, controls it to administer the prescribed volume of liquid 31 at the prescribed rate, and keeps track of its progress through the pumping cycle in respect to feedback signals provided by the Hall effect sensor and optical encoder built into motor 146, as indicated in a block 290. In addition, each of a plurality of sensors, including proximal pressure sensor 44, distal pressure sensor 56, flow detector 54, tubing detector 40, door position detector 62, and air sensor 60, listed in a sensor block 288 provide signals to CPU and memory block 282 that are used to determine the status of volumetric pump 30 and potentially harmful conditions. Power for controller 280 is supplied by a conventional power supply 294. In the event that any of the signals provided by the sensors in block 288 indicate a potentially harmful condition, such as a large air bubble or lack of fluid flow from volumetric pump 30, CPU and memory block 282 effects an alarm condition, causing both a visual and audible signal to be generated by an alarm 292, to alert medical personnel of the problem.

For purposes of recording patient history and to interface with other controllers, a data output path 296 is also optionally provided for CPU and memory block 282.

Many of the desirable characteristics of volumetric pump 30 can be achieved in a different embodiment of the volumetric pump shown generally at reference numeral 400 in FIGS. 20 and 21. A cassette for use in connection with volumetric pump 400 is generally illustrated at reference numeral 300 in FIGS. 16-19. Cassette 300 comprises a housing 302 sealed to a front panel 304, preferably made of rigid plastic. At the bottom of housing 302 are an inlet port 306 and an outlet port 308. Flexible tubing 310 is connected to inlet port 306 and may connect to container 32. Flexible tubing 312 is connected to outlet port 308 and may connect to needle/catheter 36 or other apparatus. A proximal air-in-line sensor 314 and a distal air-in-line sensor 316 are provided that engage flexible tubing 310 and 312, respectively, to detect the presence of air bubbles larger than a predetermined size within the tubing. In front panel 304 of cassette 300 are a plurality of ports, including an inlet valve port 320, a proximal pressure sensor port 324, a plunger port 330, an outlet valve port 334, and a distal pressure sensor port 338. These ports give access to a flexible membrane 340, which is disposed between front panel 304 and housing 302, overlying a plurality of fluid passages and chambers, as described below.

Cassette 300 is considered disposable and is used with volumetric pump 400 as described below. An inlet valve actuator 318 on volumetric pump 400 applies a variable biasing force to deflect flexible membrane 340 within inlet valve port 320. In proximal pressure sensor port 324, the pressure developed by fluid behind flexible membrane 340 acts upon a proximal pressure sensor rod 322, permitting the proximal fluid pressure to be sensed.

Plunger port 330 is relatively larger than the other ports, to accommodate a plunger 326, which is attached to a plunger rod 328 extending from volumetric pump 400. Plunger 326 deflects flexible membrane 340 to displace fluid behind the flexible membrane as described below. An outlet valve actuator 332 on volumetric pump 400 acts on flexible membrane 340 to control fluid flow behind the flexible membrane at outlet valve port 334, and a distal pressure sensor rod 336 detects the distal fluid pressure behind flexible membrane 340 at distal pressure sensor port 338.

In FIG. 17, a cross-sectional plan view showing the fluid passages behind flexible membrane 340 illustrates the fluid flow path through cassette 300. Fluid entering inlet port 306 flows through an inlet passage 342 and through an entry port 344 at the bottom center of a proximal pressure chamber 346. Proximal pressure chamber 346 is, of course, disposed behind flexible membrane 340 in the area defined by proximal pressure sensor port 324. A sealing ridge 348 defines the perimeter of proximal pressure chamber 346 and each of the other chambers and passages within cassette 300. Flexible membrane 340 is trapped between the top of sealing ridge 348 and the back surface of front panel 304, forming a seal that prevents fluid leakage from these chambers and passages.

A connecting passage 350 leads from proximal pressure chamber 346 into an outer channel 352, which is disposed behind inlet valve port 320. An inner ridge 354 separates outer channel 352 from a cracking chamber 356 that is disposed in the center of inlet valve port 320. As shown in FIGS. 18 and 19, inner ridge 354 is slightly lower in elevation than sealing ridge 348 and includes a nib 378 centered on its top surface. Sealing ridge 348 connects to inner ridge 354 and extends in an incline down to the lower elevational level of inner ridge 354 at the opening to a connecting passage 358. Connecting passage 358 leads into a pumping chamber 360, disposed behind plunger port 330.

From pumping chamber 360, a connecting passage 362 leads into a cracking chamber 364 at the center of outlet valve port 334. Surrouding cracking chamber 364 is an inner ridge 366, also including a nib 378 centered on its upper surface. Inner ridge 366 is slightly lower in elevation than sealing ridge 348. An outer channel 368 surrounds inner ridge 368 and is in fluid communication with a distal pressure chamber 372, which is disposed behind distal pressure sensor port 338. From the center of distal pressure chamber 372, an exit port 374 leads back into a passage 376, which runs along housing 302 and is in fluid communication with outlet port 308.

In FIG. 19, inlet valve actuator 318 is shown deflecting flexible membrane 340 sufficiently so that fluid flow over the top of nib 378 is blocked, shutting off fluid communication between central cracking chamber 356 and outer channel 352. Clearly, if the force exerted by inlet valve actuator 318 is greater than the force developed by fluid pressure within cracking chamber 356, fluid cannot flow from cracking chamber 356 into outer channel 352 past nib 378. Under this circumstance, inlet valve actuator 318 completely blocks fluid flow. However, if inlet valve actuator 318 provides a predefined cracking force to seal flexible membrane 340 against nib 378, fluid pressure within cracking chamber 356 may increase to a cracking pressure, exerting sufficient force against inlet valve actuator 318 that fluid is forced over nib 378 into outer channel 352. The same consideration applies in respect to outlet valve actuator 332 and its action on flexible membrane 340 at outlet valve port 334. Also, if inlet valve actuator 318 is drawn away from flexible membrane 340, fluid may freely flow from outer channel 352 over the top of nib 378 into cracking chamber 356.

During a filling segment of the pumping cycle for cassette 300, fluid flows freely into pumping chamber 360. During a pumpback-pressurization segment of the pumping cycle, inlet valve actuator 318 depresses flexible membrane 340 with the predefined cracking force, while plunger 326 depresses flexible membrane 340 in the pumping chamber, forcing excess fluid in the pumping chamber to flow past nib 378 and back through inlet port 306. In this pumpback-pressurization segment of the pumping cycle, outlet valve actuator 332 fully seals flexible membrane 340 against nib 378 at outlet valve port 334.

In the pumping segment of the pumping cycle, inlet valve actuator 318 applies a sealing force to fully close off fluid flow over nib 378 at inlet valve port 320, while outlet valve actuator 332 applies the predefined cracking force to flexible membrane 340 at the outlet valve port 334. Fluid is thus displaced from pumping chamber 360, flows over inner ridge 366, and through outlet port 308.

Volumetric pump 400 is generally unaffected by variations in fluid pressure at inlet port 306 or outlet port 308 of cassette 300 and delivers an accurate volumetric quantity of fluid at the desired cracking pressure, with each pumping stroke. Furthermore, since air or other gaseous fluid trapped within pumping chamber 360 cannot be compressed sufficiently to develop the cracking pressure, volumetric pump 400 is incapable of forcing fluid to flow through the outlet port if a substantial portion of the fluid within pumping chamber 360 is air or other compressible gas.

In FIGS. 20 and 21, volumetric pump 400 for cassette 300 is shown, and is in many ways similar to volumetric pump 30. Volumetric pump 400 comprises a frame 402, only a portion of which is shown. Frame 402 is adapted to mount cassette 300 in a fixed position and to apply appropriate cracking and closure forces through inlet valve actuator 318 and outlet valve actuator 332 in cooperation with the reciprocating motion of plunger rod 328, in accordance with a defined pumping cycle, to effect fluid flow through cassette 300. To simplify the disclosure of volumetric pump 400, distal and proximal pressure sensors that are connected to proximal pressure sensor rod 322 and distal pressure sensor rod 336 are not shown; however, it will be understood by those of ordinary skill in the art that proximal and distal pressure sensor rods 322 and 336 can readily be connected to pressure sensors such as strain gauges to effect sensing of fluid pressure within volumetric cassette 300.

A motor 404 is attached to frame 402 of volumetric pump 400 and includes a motor shaft 406 connected to apply a driving force to gear teeth 412 formed on one end of a cam assembly 408, via a helical gear 410. Cam assembly 408 rotates around a camshaft 414 that is mounted in bearings 472.

An inlet valve cam follower 416 in volumetric pump 400 includes a roller 420 mounted in a hood 422. Roller 420 rolls along an inlet cam track 417 formed on cam assembly 408. Inlet valve cam follower 416 is connected to a follower flexure 418, which provides a biasing force tending to keep roller 420 in contact with inlet cam track 417.

An inlet valve arm 424 is connected to inlet valve actuator 318 at a pivot pin 428, and is rotatably connected to a frame member 425 at a pivot mount 426. Acting on inlet valve arm 424 are a closure flexure 430 and a cracking flexure 432, which together combine to provide a force sufficient to fully close off fluid flow to and from inlet cracking chamber 356 in cassette 300. Closure flexure 430 acts upon a side arm 438 disposed on the side of inlet valve arm 424. Also disposed on the side of inlet valve arm 424 is a "V-shaped" arm 440. Closure flexure 430, cracking flexure 432, and inlet follower flexure 418 are all mounted to frame 402 on blocks 434, using bolts 436.

Cam assembly 408 also includes an outlet cam track 446 and a plunger cam track 442. Rotatably mounted at the end of plunger rod 328 is a roller 444, which rolls along plunger cam track 442 to reciprocally move plunger rod 328 and actuate plunger 326, thereby displacing fluid from pumping chamber 360. Plunger rod 328 is mounted on a base 480 having long longitudinally-extending arms 482 and shorter longitudinally-extending arms 486. Connected to long arms 482 and shorter arms 486 are two pairs of transversely-extending flexures 484. Flexures 484 are connected to frame 402 at each end and support plunger rod 328 just as flexures 158 support plunger 48 in volumetric pump 30. Flexures 484 also provide a biasing force to keep roller 444 in contact with plunger cam track 442.

An outlet valve cam follower 448 includes a hood 454, in which a roller 450 is rotatably mounted that rolls along outlet cam track 446. Roller 450 is biased against outlet cam track 446 by an outlet follower flexure 452. An outlet valve arm 464 is mounted to rotate about a pivot mount 466 and is pivotally connected to outlet valve actuator 332 at a pivot pin 468. A closure flexure 456 rests against a side arm 458 formed on the side of outlet valve arm 464, and in combination with a biasing force provided by a cracking flexure 460, provides sufficient force to stop fluid flow between outlet cracking chamber 364 and outer channel 368. Outlet valve cam follower 448 is actuated by outlet cam track 446 so that hood 454 deflects closure flexure 456 away from side arm 458. In this configuration, only cracking flexure 460 applies a cracking force on flexible membrane 340 through outlet valve actuator 332. Accordingly, fluid flows past inner ridge 366 when the pressure inside outlet cracking chamber 364 produces a force acting on flexible membrane 340 that exceeds the predefined cracking force of the outlet valve actuator. Outlet follower flexure 452, closure flexure 456, and cracking flexure 460 are each mounted at blocks 435 to frame 402 using bolts 436. Attached to cracking flexure 460 is a strain gauge 470 for detecting motion of outlet valve arm 464, thereby detecting fluid flow from cassette 300. Other types of sensors may be used to detect motion of outlet valve arm 464, as described in respect to outlet valve arm 180 on volumetric pump 30.

Rotation of cam assembly 408 effects sequential operation of volumetric pump 400, placing inlet valve arm 424 in an open mode, wherein plunger 326 retracts away from flexible membrane 340, allowing fluid to fill pumping chamber 360. Thereafter, the pumpback-pressurization and pumping segments of the pumping cycle proceed generally as described in respect to volumetric pump 30. It should be apparent that controller 280 (FIG. 23) is equally applicable to operation of volumetric pump 400 to pump fluid through cassette 300; however, fewer sensors are required in sensor block 288.

While the present invention has been disclosed in respect to preferred embodiments and modifications thereto, those of ordinary skill in the art will understand that further modifications may be made within the scope of the claims that follow. Accordingly, it is not intended that the claims in any way be limited by the disclosure of these preferred embodiments, but that the scope of the invention be determined entirely by reference to the claims.

The embodiments of the invention in which an exclusive property or privilege is claimed are defined as follows:

1. Apparatus for supporting a reciprocating plunger in a positive displacement pump, comprising:
   a. a frame having two spaced-apart members disposed on opposite sides of the plunger;
   b. a plurality of pairs of flexures extending between the two spaced-apart members and the plunger, said flexures having longitudinal axes, each flexure in a pair of flexures being aligned substantially parallel to the other flexure in that pair, whereby the plunger is supported by the pairs of flexures so that it can reciprocate along a reciprocation axis that is generally normal to the longitudinal axes of each pair of flexures, but is constrained by the pairs of flexures so that it does not move transversely in respect to the reciprocation axis.

2. The apparatus of claim 1, wherein the flexures are each attached to the spaced-apart members and to the plunger and apply a biasing force to the plunger directed along the reciprocation axis.

3. The apparatus of claim 2, wherein a first pair of the flexures are attached to the plunger at a first level along the reciprocation axis, and a second pair of flexures are attached to the plunger at a second level along the reciprocation axis.

4. The apparatus of claim 2, wherein a first pair of the flexures are spaced apart a first distance, and a second pair of the flexures are spaced apart a second distance that is substantially different than the first distance.

5. The apparatus of claim 1, wherein the flexures bias the plunger along the reciprocation axis against a drive force that displaces the plunger along the reciprocation axis.

6. The apparatus of claim 1, wherein one pair of flexures is spaced apart from another pair so as to prevent rotation of the plunger about a rotation axis that is normal to the reciprocation axis.

7. The apparatus of claim 1, wherein each flexure comprises an elongate, flat metal spring.

8. A method of constraining a plunger to move only along a reciprocation axis, preventing it from twisting or moving laterally away from the reciprocation axis, comprising the steps of:
   a. supporting the plunger with a first pair of flexible members that are substantially parallel and extend generally transversely to the reciprocation axis; and
   b. supporting the plunger with a second pair of flexible members that are substantially parallel and extend generally transversely to the reciprocation axis, said second pair of flexible members being spaced apart from said first pair of flexible members so that the plunger is supported thereby at spaced-apart points along the reciprocation axis, thereby preventing the plunger from twisting and moving laterally away from the reciprocation axis, yet allowing it to move along the reciprocation axis.

9. The method of claim 9, further comprising the step of spacing the first pair of flexible members apart by a substantially different distance than the second pair of flexible members to more effectively resist twisting of the plunger.

10. The method of claim 9, further comprising the steps of connecting the flexible members to opposed frame members that are spaced apart on opposite sides of the plunger, and applying a biasing force to the plunger with the flexible members, directed along the reciprocation axis.

* * * * *

UNITED STATES PATENT AND TRADEMARK OFFICE
CERTIFICATE OF CORRECTION

PATENT NO. : 5,219,279
DATED : June 15, 1993
INVENTOR(S) : V. R. Natwick et al.

It is certified that error appears in the above-identified patent and that said Letters Patent is hereby corrected as shown below:

| COLUMN | LINE | ERROR |
|---|---|---|
| Title page, item [57] Abstract | 6 | after "fluid" delete "a pumping" |
| 10 | 19 | "periostaltic" should read --peristaltic-- |
| 11 | 29 | after "the" insert --closure flexure against the side arm and thereby reducing the total force exerted-- |
| 21 | 35 | "inner ridge 368" should read --inner ridge 366-- |
| 24 (Claim 9 Line 1) | 57 | "claim 9" should read --claim 8-- |
| 24 (Claim 10 Line 1) | 62 | "claim 9" should read --claim 8-- |

Signed and Sealed this

Twenty-ninth Day of March, 1994

Attest:

BRUCE LEHMAN

*Attesting Officer*     *Commissioner of Patents and Trademarks*